US012303255B1

United States Patent
Schnan Mastronardi et al.

(10) Patent No.: US 12,303,255 B1
(45) Date of Patent: May 20, 2025

(54) VIDEO-BASED GAIT CHARACTERIZATION

(71) Applicant: GaitIQ, Inc., San Antonio, TX (US)

(72) Inventors: Barbara Schnan Mastronardi, San Antonio, TX (US); Nishanth Sivalingam, TamilNadu (IN); Joshua Pradeep, Tamilnadu (IN); Madhusoodhan Sathyanarayanan, Chennai (IN); Richard Jerome Morris, San Antonio, TX (US)

(73) Assignee: Gait IQ, Inc., San Antonio, TX (US)

( * ) Notice: Subject to any disclaimer, the term of this patent is extended or adjusted under 35 U.S.C. 154(b) by 0 days.

(21) Appl. No.: 18/627,372

(22) Filed: Apr. 4, 2024

Related U.S. Application Data

(60) Provisional application No. 63/457,071, filed on Apr. 4, 2023.

(51) Int. Cl.
*A61B 5/11* (2006.01)
*A61B 5/00* (2006.01)
*G16H 20/30* (2018.01)
*G16H 50/20* (2018.01)
*G16H 50/30* (2018.01)

(52) U.S. Cl.
CPC ............ *A61B 5/112* (2013.01); *A61B 5/1121* (2013.01); *A61B 5/1127* (2013.01); *A61B 5/743* (2013.01); *G16H 20/30* (2018.01); *G16H 50/20* (2018.01); *G16H 50/30* (2018.01)

(58) Field of Classification Search
CPC . A61B 5/11; A61B 5/107; G06T 2207/30196; G06T 2207/20084; G06T 7/20; G06T 7/60; G06T 2207/20081; G06T 2207/10016; G06T 7/70; G06T 7/246; G06T 7/73; G06V 40/25; G06V 10/82; G06V 10/34; G06V 20/647
USPC .................. 382/155, 128, 154, 224; 600/595
See application file for complete search history.

(56) References Cited

U.S. PATENT DOCUMENTS

| | | | |
|---|---|---|---|
| 10,445,930 B1 * | 10/2019 | Saylor ....................... | G06T 7/80 |
| 11,986,286 B2 * | 5/2024 | Morris ................ | A61B 5/1495 |
| 2013/0271458 A1 * | 10/2013 | Andriluka .............. | G06V 40/23 |
| | | | 345/619 |
| 2014/0024971 A1 * | 1/2014 | Bunn ................... | A61B 5/1124 |
| | | | 600/595 |
| 2016/0147959 A1 * | 5/2016 | Mariottini .............. | G16H 50/20 |
| | | | 706/46 |
| 2017/0213145 A1 * | 7/2017 | Pathak ..................... | G06N 5/04 |
| 2018/0357760 A1 * | 12/2018 | Wang .................. | G06V 10/776 |
| 2019/0110754 A1 * | 4/2019 | Rao .......................... | G06N 7/00 |
| 2021/0034846 A1 * | 2/2021 | Ko ........................ | G06N 3/082 |
| 2021/0059565 A1 * | 3/2021 | Morris .................. | G06T 7/0012 |
| 2021/0279456 A1 * | 9/2021 | Luo ........................... | G06T 7/75 |

(Continued)

*Primary Examiner* — Kathleen Y Dulaney

(74) *Attorney, Agent, or Firm* — Schwegman Lundberg & Woessner, P.A.

(57) ABSTRACT

Gait characterization and analysis based on a monocular video of a walking subject are achieved, in various embodiments, by processing the video using one or more machine-learning models to predict three-dimensional (3D) keypoint coordinates for a set of anatomical keypoints of the subject, along with joint angles, body-segment rotations, and/or gait event classifications, for multiple video frames. The machine-learning models may be trained using ground-truth data acquired with a marker-based motion capture system and/or pressure-sensitive walkway.

15 Claims, 11 Drawing Sheets

(56) References Cited

U.S. PATENT DOCUMENTS

| | | | | |
|---|---|---|---|---|
| 2021/0315486 A1* | 10/2021 | Delp | ........................ | G16H 50/50 |
| 2022/0108561 A1* | 4/2022 | Groß | ........................ | G06V 40/25 |
| 2022/0114839 A1* | 4/2022 | Qiu | ........................ | G06V 10/34 |
| 2022/0203158 A1* | 6/2022 | Tholkes | ................ | A63B 23/035 |
| 2022/0330879 A1* | 10/2022 | Faisal | ..................... | G16H 20/30 |
| 2023/0377375 A1* | 11/2023 | Tanaka | ....................... | G06T 3/60 |
| 2023/0394695 A1* | 12/2023 | Pei | ............................ | G06T 7/60 |
| 2024/0119087 A1* | 4/2024 | Yoshida | .................... | G06T 7/20 |
| 2024/0221428 A1* | 7/2024 | Lee | ........................... | A61B 5/11 |
| 2024/0363252 A1* | 10/2024 | Kumar | ................. | A61B 5/4566 |
| 2024/0378785 A1* | 11/2024 | Ishidaabe | ............... | H04N 23/60 |
| 2024/0382111 A1* | 11/2024 | Kim | ..................... | A61B 5/1121 |

* cited by examiner

VIDEO-BASED GAIT CHARACTERIZATION

CROSS-REFERENCE TO RELATED APPLICATION

This application claims priority to and the benefit of U.S. Provisional Patent Application No. 63/457,071, filed on Apr. 4, 2023, which is hereby incorporated herein by reference.

BACKGROUND

Gait—meaning a person's manner or pattern of walking or running—has been found to be a useful indicator of various clinical conditions, such as neurodegeneration, heightened fall risk, movement dysfunction, or injury. Accordingly, gait analysis is an active area of research in the medical field, bearing the promise of detecting problems (e.g., the onset of Alzheimer's or dementia) early and monitoring the efficacy of any therapy, rehabilitation after injury, or training, thus potentially improving clinical outcomes for a broad range of people, from athletes to the elderly.

Quantitative gait analysis is often performed based on measurements acquired with specialized equipment. For example, a pressure-sensitive walkway (such as, e.g., GAITRite® available from CIR Systems, Inc., Franklin, NJ) can be used to determine the time and location of various gait events occurring during a gait cycle, such as "heel strike" (i.e., the heel hitting the ground), "heel off" (i.e., the heel lifting off the ground), and "toe off" (i.e., the toe lifting off the ground), from which gait parameters such as step size, gait speed, etc. can be computed. Further, three-dimensional (3D) motion capture systems can be used to measure, more comprehensively, the configuration of the person's lower extremities or body as a whole during walking, e.g., in terms of joint locations and angles. Such systems often utilize synchronous video streams from multiple cameras positioned at different angles relative to the person, sometimes in conjunction with markers worn by the person; a commercial example of a marker-based system is the Vicon® motion capture system by Vicon Motion Systems (headquartered in Yarnton, Oxfordshire, UK). Reliance on such specialized and often complex equipment limits the availability of gait analysis to, essentially, laboratory settings. It would be desirable to provide tools for gait analysis that dispense with the need for complex hardware and cumbersome measurement processes, making gait analysis available more broadly, conveniently, and/or at lower cost.

SUMMARY

Described herein are systems and methods for video-based gait characterization and analysis. In particular, in various embodiments, the motion of a walking person (hereinafter the "subject") is quantitatively characterized based on monocular video input—i.e., a temporal sequence of video frames taken by a single video camera installed at a fixed location. The video input is processed by a suitable computing device or system to determine time-dependent three-dimensional (3D) coordinates of anatomical "keypoints" (such as, e.g., joints, body center, etc.) of the subject, which in turn enable the computation of time-dependent gait kinematic parameters associated with individual joints and body segments (e.g., joint angles and body-segment rotations) and the detection and classification of gait events (e.g., heel strike, toe-off) along with the phases within the gait cycle (hereinafter "gait phases") that these gait events demarcate. The time-dependent gait kinematic parameters and detected gait events may flow into computations of high-level statistical gait parameters, which may include, e.g., spatiotemporal gait parameters such as stride length, step length, or average velocity, as well as more complex gait metrics characterizing gait variability, symmetry, and quality; in various applications, these parameters and metrics serve as indicators of certain clinical conditions and/or as physical performance metrics. Further, in conjunction with the identified gait phases, the time-dependent gait kinematic parameters may be used in advanced, more detailed phase-specific gait analysis, e.g., to assess whether the subject's gait differs, in terms of one or more gait kinematic parameters during one or more gait phases, from a reference population; large deviations of the subject's gait kinematic parameters from the reference data in any of the gait phases may be indicative of a disorder. Such analysis may serve not only to detect gait abnormalities and disorders, but also to select a suitable therapeutic intervention, e.g., physiotherapy targeted at the specific muscle(s) or muscle group(s) associated with the abnormal gait phase(s).

By enabling gait characterization and analysis based on monocular video input, the disclosed approach significantly reduces hardware requirements, and thus cost and complexity, as compared with many conventional motion captures systems like marker-based or multi-camera systems. In general, the monocular video may be acquired by any digital camera, including, for instance, the integrated camera of an electronic tablet, smartphone, or similar mobile device. The same device may also provide some or all of the processing functionality for computing the keypoint coordinates and downstream gait parameters and metrics and performing associated analyses. Alternatively, the video data itself or data derived therefrom by partial processing may be transferred, via a wired or wireless connection, to a separate computing system, such as a cloud-based server computer, for further processing. Either way, in view of the ubiquity of mobile devices, the methods disclosed herein, unlike many prior-art systems, are not limited in practice to laboratory settings, but can be implemented in almost any environment. As a result, they facilitate wide-spread adoption of gait analysis as a diagnostic tool, e.g., across medical care settings.

The computing device or system may process the video input in a "pipeline" of processing modules that includes one or more machine-learning models—that is, computational models trained on data, rather than explicitly programmed, to perform a specified task. At the first stage of the pipeline, a two-dimensional (2D) keypoint model operates on the video input to compute, for each frame, the 2D coordinates of a first set of anatomical keypoints of the subject. These 2D coordinates of the anatomical keypoints (hereinafter also "2D keypoint coordinates," or "2D keypoints" for short) flow as input into a 3D keypoint model at the second stage, which computes, for each frame, 3D coordinates for a second set of anatomical keypoints (hereinafter also referred to as "3D keypoint coordinates," or "3D keypoints" for short). Both the 2D keypoint model and the 3D keypoint model may include sub-models that compute 2D or 3D keypoints separately for different parts of the body (e.g., main body, pelvis, foot). The first and second sets of anatomical keypoints may be the same or may differ, but they typically overlap in the anatomical keypoints they contain. In some embodiments, the second set is larger than the first, including not only 3D counterparts of the 2D keypoints of the first set, but also additional 3D keypoints predicted from the 2D keypoint coordinates of nearby anatomical keypoints. At the third stage, one or more gait models compute, from input including some or all of the 3D keypoints, gait kinematic parameters such as joint angles and/or body-segment rotation angles (herein also simply "body-segment rotations"), and/or predict gait events associated with the start and end of foot contact with the floor (hereinafter also "gait contact events" or simply "contact events"). In various embodiments, the 2D keypoint model, 3D keypoint model, and gait models of the pipeline are implemented by machine-learning models, e.g., neural networks. In the fourth processing stage, the output of the gait kinematic parameters and gait events output by the gait models the third stage may be further processed, e.g., to compute statistical gait parameters characterizing the gait or stride as a whole, and/or to label video frames by gait phase followed by phase-specific analyses.

The various machine-learning models of the pipeline may be trained in a supervised manner, e.g., using ground-truth labels obtained with conventional gait analysis equipment. For example, to train the 3D keypoint model, ground-truth 3D keypoint coordinates may be obtained with a marker-based motion capture system in conjunction with a biomechanical model that converts marker coordinates to the 3D coordinates of the anatomical keypoints of the second set. Similarly, ground-truth joint angles and body-segment rotations to train the respective gait models of the third stage may be computed with the biomechanical model from the marker coordinates. Ground-truth labels for training a gait model to predict gait contact events may be determined with a pressure-sensitive walkway. The ground-truth data for each model is acquired simultaneously, and correlated frame by frame, with the monocular video that serves as input to the machine-learning pipeline in the training phase for the respective model. For efficiency, training data for multiple or all of the models may be acquired simultaneously in a single procedure. For instance, video data may be acquired while a subject wearing markers is walking on a pressure-sensitive walkway, for simultaneous video acquisition, marker-based motion capture, and gait-event measurements. Once the machine-learning models have been trained, pressure-sensitive walkways, markers, and multi-camera systems can be dispensed with, and the trained pipeline can operate on the video stream of a single camera.

Beneficially, by operating different models on the same video input, the processing pipeline can compute outputs of different types, such as gait kinematic parameters and gait contact events, that are inherently synchronized, facilitating more advanced computations and analyses that process the different types of outputs in conjunction. If the same outputs were instead obtained using multiple different hardware systems, such as a marker-based motion capture system and a pressure-sensitive walkway, using them in conjunction would be contingent on complex synchronization procedures that may or may not be practically feasible. Accordingly, in addition to lowering the cost and complexity of gait analysis, quantitatively characterizing a subject's gait based on the video input from a single camera can also enable new analytic functionality.

The accuracy of the results output by the machine-learning model(s) generally depends, among other things, on the fidelity with which the placement and orientation of the video camera relative to the walking path that was used during training of the model(s) are reproduced during later deployment of the trained model(s). In various embodiments, therefore, a practical, easy-to-use method for high-fidelity camera placement and alignment is provided for improved accuracy. This alignment method utilizes a software application, e.g., an app installed on the same mobile device as is used to acquire the video, that guides an end user (e.g., medical personnel acquiring video data of a patient) through the process. The app may, for example, display, overlaid onto the camera view, a 2D projection of a 3D outline defining the walking path and the "walking volume" thereabove that are to be traversed by the subject (e.g., patient) in the inference phase if the relative camera configuration of the training phase are to be reproduced. The mobile device can then be positioned and oriented relative to the actual walking volume used in the inference phase to ensure that they coincide with the displayed outline.

This summary of various aspects and features of the disclosed subject matter serves to provide an overview and introduce important concepts, but is in no way intended to require that all aspects and features are used together or to limit the scope of the disclosure to certain specific embodiments. Rather, the various aspects can generally be employed independently of one another, and not all of the above-described features need be present in each embodiment. For example, not all embodiments include gait-event detection, and not all embodiments that do include gait-event detection further involve phase-specific analysis. Or, as another example, camera alignment need not necessarily utilize an outline overlaid onto a camera view, and conversely, the disclosed camera alignment method may be beneficial in applications other than those described herein.

BRIEF DESCRIPTION OF THE DRAWINGS

The foregoing summary of various aspects and features of the disclosed systems and methods for video-based gait characterization and analysis will be more readily understood from the following detailed description of example embodiments, in particular, when taken in conjunction with the accompanying drawings.

FIGS. 9A and 9B are schematic perspective views illustrating the location of the subject relative to the walking volume at the beginning and end of an example walking path if the camera is properly aligned, while

FIG. 8 is a schematic drawing of example hardware implementing a system for video-based gait characterization and analysis in accordance with various embodiments.

DESCRIPTION

Figure 1:
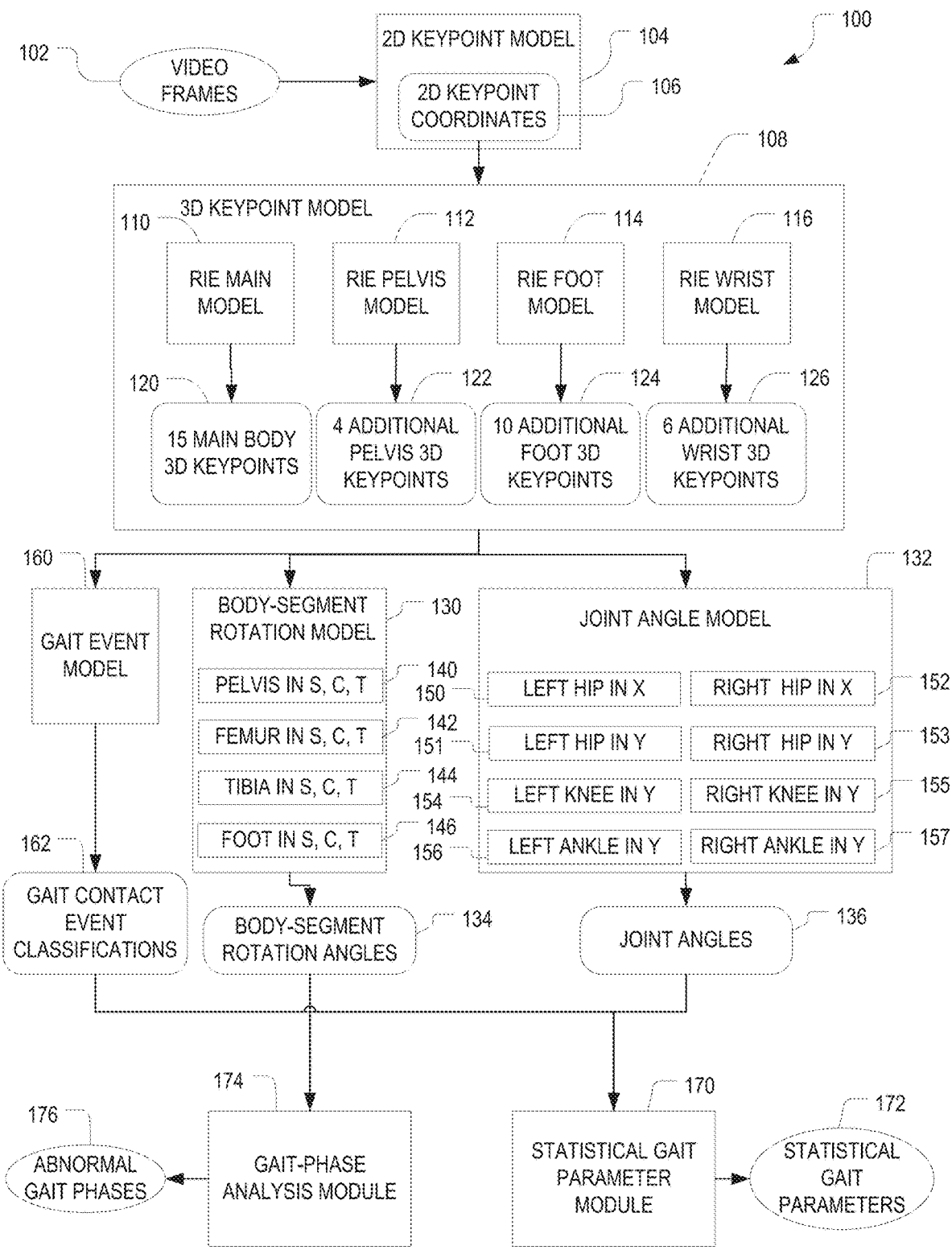
FIG. 1 is a block diagram illustrating a processing pipeline for video-based gait characterization and analysis in accordance with various embodiments.
Figure 2:
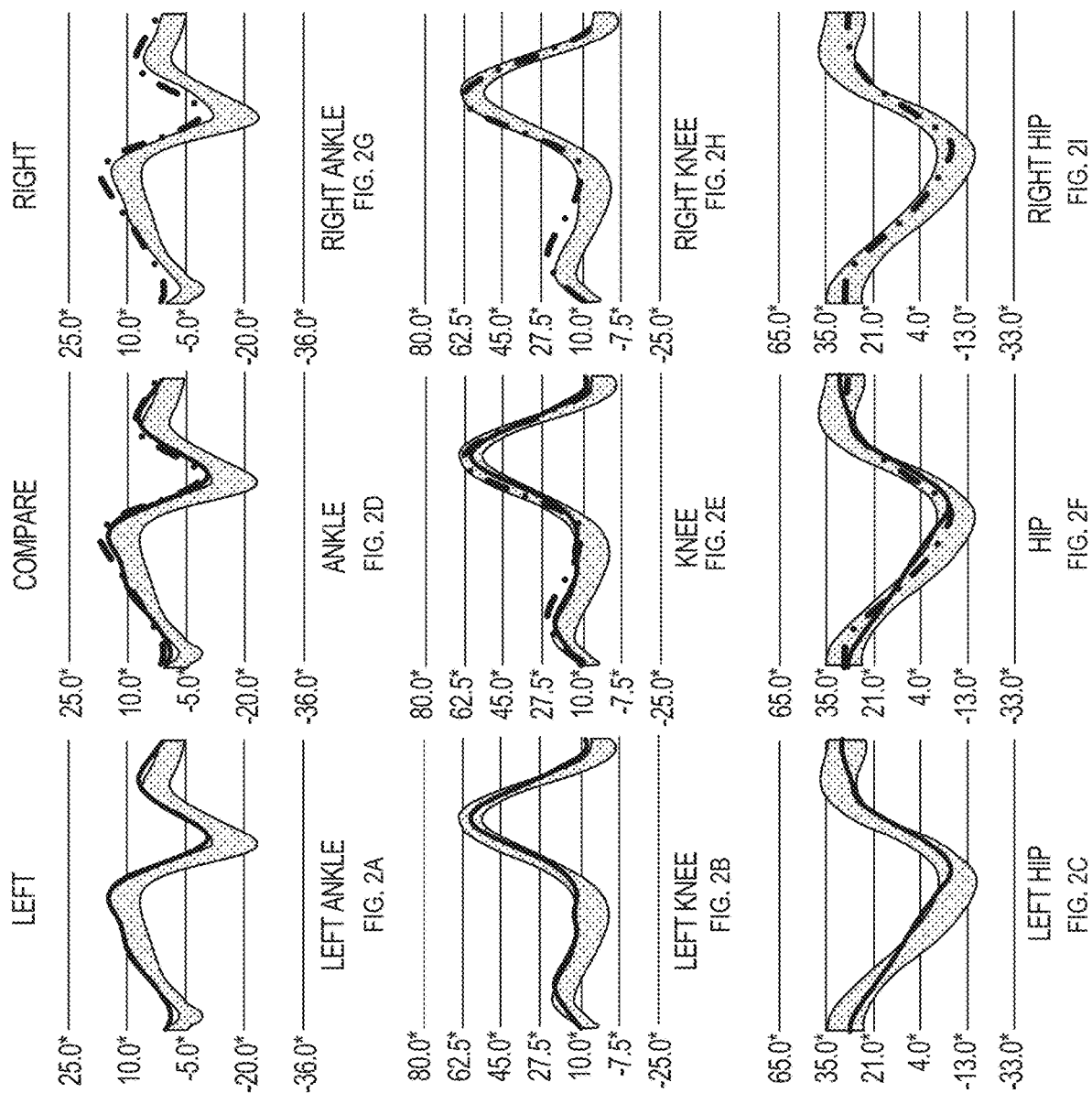
FIGS. 2A-2I are example graphs illustrating various time-series gait kinematic parameters predicted from 3D keypoints in accordance with various embodiments.

FIG. 1 is a block diagram illustrating a processing pipeline 100 for video-based gait characterization and analysis in accordance with various embodiments. Input to the pipeline 100 is a video, composed of a sequence of video frames 102 (each frame corresponding to one image) taken by a digital camera at a suitable frame rate, e.g., at 50 Hz. The camera may be a CCD (charge-coupled device) or CMOS (complementary metal-oxide semiconductor) sensor camera, as are known in the art, and may be a provided as a stand-alone device, or integrated, e.g., in an electronic tablet, smartphone, or other mobile device. Either way, the camera may be connected, via a wired connection or wirelessly, to a computing device or system (herein also a "processing facility") that processes the video frames and implements the machine-learning pipeline, using a suitable combination of computational hardware and/or software. The processing facility may be, for example, a computer or computer cluster including one or more general-purpose hardware processors that execute instructions stored in computer-readable memory. Alternatively, some or all of the computational functionality of the pipeline 100 may be provided by special-purpose processors or circuitry, such as by one or more digital signal processors (DSPs), application-specific integrated circuits (ASICs), field-programmable gate arrays (FPGAs), or graphic processing units (GPUs). In some embodiments, the camera and processing facility are provided by the same device, e.g., a smartphone.

The video frames 102 may have undergone pre-processing, e.g., by image cropping, resizing, noise filtering, color or brightness correction, and/or similar operations in a suitable combination. In one embodiment, such preprocessing involves, first, detecting the subject and defining a bounding box around the subject within each frame of the original video output of the camera, and then cropping each video frame based on the respective bounding box. The cropped images, which generally differ in size from frame to frame (e.g., as a result of the subject walking towards the camera during video capture), may be padded to achieve a desired aspect ratio, and resized by interpolation to obtain the desired number of pixels. The images can then be pixelwise normalized based on the means and standard deviations of their RGB color values.

The (pre-processed) video frames 102 flow, at the first stage of the processing pipeline 100, into a 2D keypoint model 104, implemented by one or more machine-learning (sub-)models, that determines the 2D coordinates 106 of a specified first set of anatomical keypoints on the subject within each video frame. Suitable machine-learning models and respective software implementations are readily available, including in existing open-source code.

In one embodiment, the 2D keypoint model 104 includes two pre-trained open-source 2D keypoint (sub-)models: an HRNet (High-Resolution Net) and a MediaPipe model. HRNet is a convolutional neural network for task including object detection and image classification, which is able to maintain high-resolution representations throughout the whole process and has been applied to the problem of human pose estimation in implementations known in the art as deep High-Resolution Representation Learning for Human Pose Estimation. In one example, the HRNet model comes pretrained on the MS COCO (Microsoft Common Objects in Context) dataset and is used in the processing pipeline 104 to compute, from each input image in the sequence of video frames 102, high-precision 2D keypoint coordinates (e.g., specified in pixels in the x, y directions) for the following fourteen anatomical keypoints: head (midpoint of right and left eye), left shoulder, right shoulder, left elbow, right elbow, left wrist, right wrist, left hip, right hip, left knee, right knee, left ankle, right ankle, and pelvis (midpoint of right and left hip). The MediaPipe model is used, in this embodiment, to supplement the 2D keypoints output by the HRNet model with the 2D keypoint coordinates for the following additional anatomical keypoints: right heel, left heel, right foot index toe, left foot index toe, right hand little finger (fifth digit), left hand little finger. It has been found that adding these anatomical keypoints to the first set of anatomical keypoints, for which 2D keypoint coordinates are computed in the first stage of the processing pipeline 100, improves the computation of 3D keypoints in the second stage.

In another embodiment, the 2D keypoint model 104 is implemented by the ViTPose model, a vision transformer model adapted to human pose estimation that is described in detail in arXiv publication No. 2204.1248v3, and has been implemented in open-source code available, e.g., on GitHub. ViTPose outputs heatmaps, e.g., matching the spatial resolution of the underlying (pre-processed) video input, that signify for each pixel the probability that a specified target anatomical keypoint is present. Generating and analyzing heatmaps for a set of target keypoints corresponding to all of the anatomical keypoints within the first set of anatomical keypoints allows locating the anatomical keypoints in the pre-processed images. To determine consistent 2D coordinates 106 for the anatomical keypoints across all frames, the keypoint predictions computed for the pre-processed images (e.g., as result from cropping, etc. as described above) are then mapped back to the original video frames by applying suitable scaling and translation operations. In some embodiments, ViTPose is used to directly compute 2D keypoint coordinates 106 for the following twenty anatomical keypoints: right hip, left hip, right knee, left knee, right ankle, left ankle, right shoulder, left shoulder, right elbow, left elbow, right wrist, left wrist, right heel, left heel, right first metatarsal, left first metatarsal, right fifth metatarsal, left fifth metatarsal. Further, 2D keypoint coordinates for the following four additional anatomical keypoints are created by interpolation: pelvis, right hand, left hand, head.

The 2D keypoint coordinates 106 flow as input into a 3D keypoint model 108, implemented by one or more machine-learning (sub-)models, that determine the 3D coordinates of a second specified set of anatomical keypoints on the subject. This second set of anatomical keypoints is generally different from, although it may significantly overlap with, the first set of anatomical keypoints. That is, at this second stage of the processing pipeline 100, the 2D keypoints are not simply converted one by one into 3D keypoints, but are used collectively to inform the computation of 3D keypoints, which may include 3D coordinates of anatomical keypoints not included in the first set, resulting in a set of 3D keypoints that is larger than the set of 2D keypoints based on which it is predicted. A given 3D keypoint is generally computed from the corresponding 2D keypoint—if one is available—along with a set or cluster of nearby 2D keypoints. For example, in one embodiment, 2D keypoints associated with the foot include only the ankle, first metatarsal, and fifth metatarsal. This cluster of 2D keypoints can be leveraged to not only compute the counterpart 3D keypoints, but additionally 3D keypoints for the lateral ankle and mid-foot points. To determine which 2D keypoints to include in the cluster, multiple training runs may be conducted during the training phase to assess the impact of various 2D keypoints on the prediction of a target 3D keypoint, and the highest-performing set of 2D keypoints may be selected. In addition to using potentially multiple 2D keypoints to determine a given target 3D keypoint, the target 3D keypoint for a given video frame may be computed from the 2D keypoints on multiple video frames (generally the given video frame and a few frames that precede and/or follow it in the sequence) to take advantage of temporal interdependencies.

In the depicted example, the 3D keypoint model 108 includes four 3D keypoint sub-models 110, 112, 114, 116 that are used to separately compute 3D keypoint coordinates of anatomical keypoints associated with four general anatomical regions: the main body, the pelvis, the feet, and the wrists. All four models may be deep neural network models, such as Robust Information Encoding (RIE) models. In one example, the main body model 110 computes 3D keypoint coordinates for: pelvis, right hip, right knee, right ankle, left hip, left knee, left ankle, thorax, head, left shoulder, left elbow, left wrist, right shoulder, right elbow, and right wrist (collectively fifteen main body 3D keypoints 120); the pelvis model 112 computes 3D keypoint coordinates 122 for: left anterior pelvis, right anterior pelvis, left posterior pelvis, and right posterior pelvis (collectively four additional pelvis 3D keypoints 122); the foot model 114 computes 3D keypoint coordinates for: left heel, left foot (mid-foot point), left lateral ankle, left first metatarsal, left fifth metatarsal, right heel, right foot (mid-foot point), right lateral ankle, right first metatarsal, and right fifth metatarsal (collectively ten additional foot 3D keypoints 124); and the wrist model computes 3D keypoint coordinates for: left hand, left radius, left ulna, right hand, right radius, and right ulna (collectively six additional wrist 3D keypoints). Together, the four models 110, 112, 114, 116 compute a total of thirty-five 3D keypoints 120, 122, 124, 126.

The 3D keypoints (e.g., 120, 122, 124, 126) flow into one or more gait models at the third stage to generate outputs that quantitatively characterize the subject's gait. As depicted, these models may include a body-segment rotation model 130 and a joint angle model 132 (collectively also referred to as "gait kinematic models"). Each of these models 130, 132 may be implemented by one or more machine-learning (sub-)models, such as by deep learning models based on Long Short-Term Memory (LSTM) architectures. To compute body-segment rotation angles 134 and joint angles 136 for a given frame, the models 130, 132 may process a series of frames (including the frame at issue) to take advantage of temporal information.

The body-segment rotation model 130 computes, from the 3D keypoints (or a subset thereof), rotation angles 134 (e.g., in degrees) of various body segments for the three anatomical planes: the sagittal, coronal, and transverse planes (S, C, T). To define the anatomical planes for the subject as a whole in an orthogonal "world coordinate system," let the z-axis extend vertically, the x-axis extend horizontally in the walking direction, and the y-axis extend horizontally in a direction perpendicular to the walking direction. Then, the sagittal plane corresponds to the x-z plane; the coronal plane corresponds to the y-z plane; and the transverse plane corresponds to the x-y plane. The anatomical planes for each of the body segments are defined in terms of separate coordinate systems (with axes x', y', z') fixed relative to the respective body segment. For a body segment extending between proximal and distal joints (e.g., the tibia, which extends from the knee joint to the ankle joint), the line connecting these two joints defines the z'-axis. The x'-axis or y'-axis, depending on the particular body segment, is defined as an axis perpendicular to both the z'-axis and the line connecting medial and lateral points defined on the body segment (at a common value of z'), where the medial and lateral points correspond to points closer to and farther away from the axis of the body, respectively. For example, for the right tibia, the medial point is located on the left side of the tibia and the lateral point is located on the right side of the tibia, and the connecting line is chosen to correspond to the y'-axis; the x'-axis is then determined as an axis perpendicular to both the z'-axis and the y'-axis. For the left or right foot, the connecting line between the medial point closer to the heel and the lateral point closer to the toes defines the x'-axis, and then the y'-axis is determined as perpendicular to the x'-axis and the z'-axis. Given the body-segment-specific x'-y'-z' coordinate systems, the sagittal, coronal, and transverse planes associated with the body segment corresponds to the x'-z' plane, the y'-z' plane, and the x'-y' plane, respectively. The body-segment rotation angles, which capture rotations of a body segment relative to the body at large, are defined as the angle enclosed between the x and x' axes, the angle enclosed between the y and y' axes, and the angle enclosed between the z and z' axes.

In the depicted example, the body-segment rotation model 130 uses four sub-models 140, 142, 144, 146 compute body-segment rotation angles separately for the pelvis, femur, tibia, and foot, respectively. In general, body segment rotations are not fully determined in three dimensions by the 3D locations of their adjacent proximal and distal joints, and therefore cannot be straightforwardly calculated from the associated 3D keypoint coordinates. For example, while the 3D keypoint coordinates of the knee and ankle determine the orientation of the z' axis along the tibia within the x-y-z world coordinate system, they do not allow inferring the rotation of the tibia about the z' axis. Thus, if the tibia is, for instance, oriented vertically (such that the rotation angle between z and z' is zero), the rotation of its coronal plane relative to the coronal plane of the world coordinate system (depicted in FIG. 7B described below), as captured in the angle between the y- and y'-axes, is not determinable from the 3D keypoints of the adjacent joints. However, using a machine-learning model operating on a larger set of 3D keypoints (e.g., including, but not limited to the adjacent joints), and trained on data that does include full 3D body-segment rotation information (as discussed in more detail below), it is possible to nonetheless predict all three rotation angles for the tibia. The determination of body-segment rotations is also aided, in some cases, by the availability of 3D keypoints beyond those having counterparts in the set of 2D keypoints. For example, for the pelvis, rotations in the transverse plane about the z-axis and rotations in the coronal plane about the x-axis (the latter being associated with pelvic obliquity) could in principle be determined from the locations of the left and right hip joints, but the pelvis rotation in the sagittal plane about the y-axis, corresponding to pelvic tilt, is not determinable from hip joint coordinates and/or center pelvis coordinates. In some embodiments, however, the pelvis sub-model 112 of the 3D keypoint model 108 provides additional 3D keypoints on the pelvis, such as keypoints associated with the left anterior pelvis (more precisely, the left anterior superior iliac spine (ASIS)), right anterior pelvis (or, more precisely, right ASIS), left posterior pelvis (more precisely, the left posterior superior iliac spine (PSIS)), and right posterior pelvis (or, more precisely, right PSIS), which facilitate determining pelvic tilt. Even in this case, however, predicting the rotation angles of the pelvis with a machine-learning model operating on a larger set of 3D keypoints (rather than directly calculating them based on a minimal set of 3D keypoints) may be beneficial, e.g., to improve accuracy. Accordingly, the disclosed machine-learning-based approach, by increasing the number of available 3D keypoints and/or processing larger sets of 3D keypoints in conjunction, facilitates determining body segment rotations that, without such models, would not be calculable from video input alone.

The joint angle model 132 computes, from the 3D keypoints (or a subset thereof), the angles 136 of various joints about the x, y, and/or z axes (e.g., depending on the type of joint). In the depicted example, eight separate models 150, 151, 152, 153, 154, 155, 156, 157 compute the 2D angles of the left hip about the x and y axes (the horizontal axes) (models 150, 151), the 2D angles of the right hip about the x and y axes (the horizontal axes) (models 152, 153), the one-dimensional (1D) angle of the left knee about the y axis (model 154), the 1D angle of the right knee about the y axis (model 155), the 1D angle of the left ankle about the y axis (model 156), and the 1D angle of the right ankle about the y axis (model 157). The joint angle(s) for a given joint may in principle be computed from the 3D keypoint coordinates associated with the two adjacent joints. For instance, the joint angle associated with the knee may be determined by the 3D locations of the corresponding hip and ankle. However, with a machine-learning model that generally uses more than two adjacent joint and optionally takes temporal information into account when computing joint angles, the accuracy can be improved.

The third processing stage may further include a gait event model 160 that detects, based on the 3D keypoints output by the second stage for each frame, certain gait contact events defined based on the foot (or part of the foot) making contact, or ceasing contact, with the floor. These contact events may include left foot strike, right foot strike, left foot off, and right foot off. Accordingly, in some embodiments, the gait event model provides, for each frame in the video, a five-fold classification indicating whether any of these four gait contact events, or none, occurred. Optionally, a distinction may further be made between heel off and toe off, for a total of six gait contact events (namely, left foot/heel strike, right foot/heel strike, left heel off, right heel off, left toe off, or right toe off) and a seven-fold classification. Based on the gait contact event classification 162 for each frame, gait contact events of a given type can be associated with specific frames and/or their associated time stamps. The gait contact event classification 162 may be categorical or, alternatively, probabilistic. In a probabilistic classification, the output for each frame is a probability distribution that assigns each of the possible (e.g., five or seven) events (including no event) a probability that the respective event occurred (with all five or seven probabilities summing up to one). The gait event model may be implemented using a deep learning neural-network model with a custom ResGCN (Residual Graph Convolutional Network) and multiple dense (fully connected) network layers towards the end. Instead of classifying each frame based on the 3D keypoints of that frame only, temporal information may be taken into account by determining the gait event for a given frame based on the 3D keypoints of a series of frames (e.g., thirty frames, including the frame to be classified in terms of gait events). In this way, the accuracy of the gait event prediction can be significantly improved.

While the body-segment rotation, joint angle, and gait event models 130, 132, 160 of the third processing stage independently determine, from the 3D keypoints, different qualitative and quantitative gait information that can be useful in and of itself, the processing pipeline 100 may include a fourth stage at which the 3D keypoints of the second stage, along with the body-segment rotations, joint angles, and gait contact event classifications 160 output by the third-stage models are further processed in conjunction with each other in various combinations to provide richer and/or more detailed information.

In particular, in various embodiments, gait events are used not only to segment the time-series data into multiple gait cycles, but also to segment individual gait cycles into their distinct phases. A gait cycle, viewed from the perspective of one foot, starts and ends with the heel of that foot touching the ground, completing a stride that includes both feet. The cycle comprises two main phases: the stance phase, where the foot is on the ground, and the swing phase, when the foot is airborne. The stance phase begins with the initial contact made by the heel, and unfolds through loading response, mid-stance, terminal stance, and a pre-swing phase ending when the toe comes off the ground, while the swing phase begins with toe off, and progresses through initial swing, mid-swing, and terminal swing, culminating in the next heel strike (see FIG. 3 for an illustration). These phases and events orchestrate the complex dynamics of coordination, balance, and propulsion in walking.

The gait phases are demarcated by gait events, which include both the contact events detected with the gait event model 160, as well as certain events defined in terms of body segment rotations and joint angles. Table 1 below describes a full gait cycle for the right leg and foot, and associates each phase with the gait events that constitute its start and end points. In addition to gait contact events including the heel-strike and toe-off events of both feet, the gait events used in segmenting the gait phases include the maximum right knee flexion, which can be ascertained from the time-dependent knee joint angle (that is, the output of joint angle sub-model 155), as well as the right heel rise and vertical orientation of the right tibia, which can be determined from the time-dependent rotation angles of the right foot in the transverse plane and the right tibia in the sagittal plane, respectively (which are included in the output of body-segment rotation sub-models 146, 144).

TABLE 1

| Gait Main Phase | Gait Phase | Start of Gait Phase | End of Gait Phase |
|---|---|---|---|
| Stance Phase | Loading Response | Right Heel Strike | Left Toe Off |
| | Mid-Stance | Left Toe Off | Right Heel Rise |
| | Terminal Stance | Right Heel Rise | Left Heel Strike |
| Swing Phase | Pre-Swing | Left Heel Strike | Right Toe Off |
| | Initial Swing | Right Toe Off | Max. Right Knee Flexion |
| | Mid-Swing | Max. Right Knee Flexion | Vertical Right Tibia |
| | Terminal Swing | Vertical Right Tibia | Right Heel Strike |

The fourth stage may include a module 170 for computing various higher-level statistical gait parameters 172, such as spatiotemporal parameters or complex measures of gait variability, symmetry, overall quality or other aspects of the gait. Spatiotemporal parameters may be computed from the time-dependent 3D joint positions (which are, along with joint angles and body-segment rotations, an example of gait kinematic parameters), corresponding to 3D keypoint coordinates associated with the joints, in conjunction with gait (contact) events used to dissect the time-series data into distinct strides, steps, or phases within the gait cycles. Spatiotemporal parameters include, for example and without limitation, averages or variabilities (e.g., standard deviations or variances) over generally multiple gait cycles of: walking speed (e.g., measured in cm/s), cadence (e.g., measured in steps per minute), stride length (spatial distance between two successive heel strikes with the same foot, e.g., measured in cm), step length (spatial distance between adjacent heel strikes of the left and right feet, e.g., measured in cm), swing time (duration of the swing phase as a fraction of the duration of the gait cycle, e.g., in %), or double-support time (duration of the pre-swing phase between heel strike of one foot and toe off of the other foot, where both feet are simultaneously on the ground, as a fraction of the duration of the gait cycle, e.g., in %). Among the more complex gait metrics, are the normalized symmetry index (NSI), margin of stability (MOS), and gait profile score (GPS). The NSI measures the level of symmetry between left and right limbs, with a value of zero corresponding to perfect symmetry and a maximum value of one hundred representing "perfect asymmetry," and is computed from joint angles, body-segment rotations, and gait events. The MOS measures the subject's medial-lateral and anterior-posterior stability while walking, and is computed from 3D keypoint coordinates of the joints and gait events. The GPS is a clinical index that can be used to measure the overall deviation of gait data relative to normative data, and is computed from joint angles, segment rotations, and gait events. Yet another category of complex statistical gait parameters are entropy metrics (e.g., Sample Entropy, Multi-Scale Entropy, or GaitSD) defined to measure the degree of stride-to-stride variability in the characteristic shapes of the time-dependent gait kinematic parameters (which include joint positions, joint angles, and body-segment rotations).

The fourth processing stage may further include a gait-phase analysis module 174 that analyzes gait kinematic parameters (including, e.g., joint angles 136, body-segment rotation angels 134, and joint positions included in the 3D keypoint coordinates) separately for each phase of the gait, and compares the phase-specific metrics against corresponding reference data to identify any abnormal gait phases 176 and quantity the degree of abnormality. For this purpose, the gait-phase analysis module 174 uses gait event data, including the gait contact event classifications 162 of each frame and other relevant gait events derived from the joint angles 136 and body-segment rotation angle 134 (e.g., heel rise, maximum knee flexion, and vertical tibia events), to label each frame with the gait phase to which it belongs. The ability to simultaneously predict of gait events and gait phases as well as gait kinematic parameters like joint angles and body-segment rotations in each frame of the monocular video, along with existing knowledge of which muscle groups are active at each phase of the gait cycle, facilitates evidence-based diagnosis of complex gait disorders without the need for specialty equipment in the clinic, and furthermore provides clinicians with the capability to prescribe and monitor targeted exercise and therapeutic interventions to improve outcomes. The muscle groups that are active during each phase of gait are known to practitioners; therefore, knowing the biomechanical measurements during specific phases of gait can help guide clinicians to specific actions such as eccentric, concentric, or isometric exercises of specific muscle groups. The biometrics help guide the clinician assign specific International Classification of Diseases (ICD) codes for medical records such as ICD-10 M21.371.

FIGS. 2A-2I are example graphs illustrating various time-series gait kinematic parameters predicted from 3D keypoints in accordance with various embodiments. In particular, the joint angles associated with the left (FIGS. 2A-2C) and right (FIGS. 2G-2I) ankles, knees, and hips are shown over a full gait cycle, along with a left-right comparison (FIGS. 2D-2F) that may serve to characterize gait symmetry. In addition to the time-dependent joint angles for the test subject (e.g., a particular patient), FIGS. 2A-2I also depict bands (stippled) indicating the statistical distribution of the time-dependent joint angles for a reference population deemed normative (e.g., a group of individuals with healthy gait). Comparisons of the test subject's joint angles against this reference data allows assessing the degree of normalcy of the subject's gait both visually (qualitatively) and mathematically (quantitatively).

Figure 3:
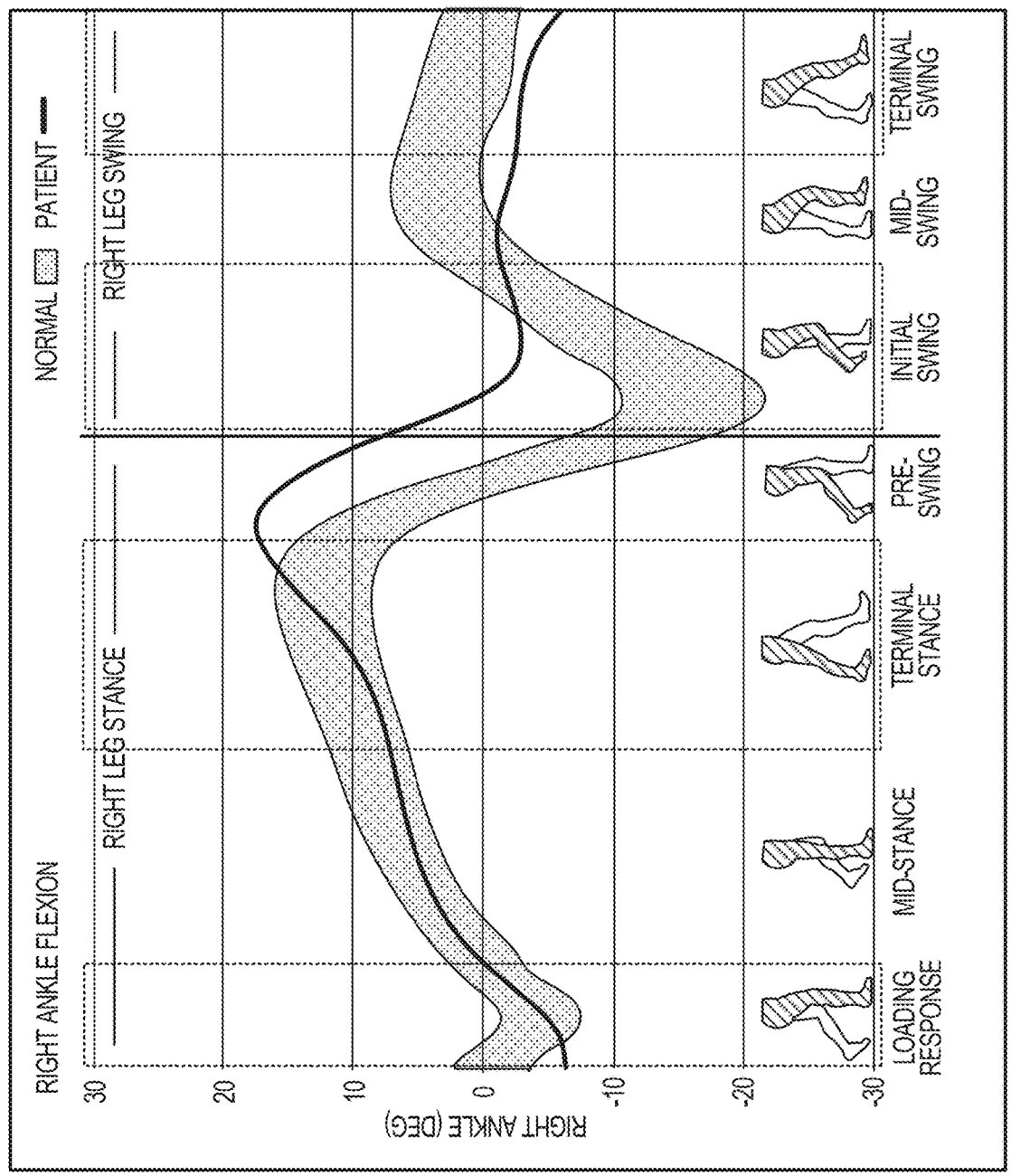
FIG. 3 is an example graph illustrating phase-based gait analysis in accordance with various embodiments.

FIG. 3 is an example graph illustrating phase-based gait analysis in accordance with various embodiments. The graph shows the time-dependent right ankle flexion (i.e., the joint angle associated with the right ankle) over the course of one gait cycle, which is segmented into the seven distinct gait phases described above. Along with a curve representing the right ankle flexion of the subject (e.g., patient), the distribution of right ankle flexion of a reference group is shown as a stippled band. The reference group may be representative of the population at large, or of relevant population group, e.g., including people of similar age as the patient that possess a healthy, or normal, gait. For each of the gait phases, the patient data may be compared with the reference data. For example, the curves may be sampled at event time intervals, e.g., a hundred intervals over the full gait cycle, and the difference between the patient's ankle flexion and the average ankle flexion of the reference group (e.g., corresponding to the mid-line of the depicted band) may be computed for each sampled point in time, and averaged over the samples within each gait cycle. The average difference, or deviation, for each gait cycle can then be normalized by the standard deviation (represented by the width of the stippled band) associated with the reference data within that cycle.

In the depicted example, which illustrates the kinematic analysis for an 82-year-old man reporting falls, the greatest deviation between patient and reference data, amounting to 3.1 standard deviations, occurs in the pre-swing and initial swing phases. Smaller deviations of 1.2 and 1.3 standard deviations are present in the mid-swing and terminal swing phases, respectively. In the loading response, mid-stance, and terminal stance phases, on the other hand, the patient's ankle flexion is within a standard deviation of the mean of the reference distribution. The muscle group involved in all four phases where deviations occur is the pretibial muscles. During the pre-swing, initial swing, and mid-swing, these muscles undergo concentric contractions, whereas the terminal swing phase is associated with isometric contractions. Accordingly, a targeted treatment addressing the diagnosed gait disorder focuses on strengthening the pretibial muscles, including both concentric and isometric exercises.

Figure 4:
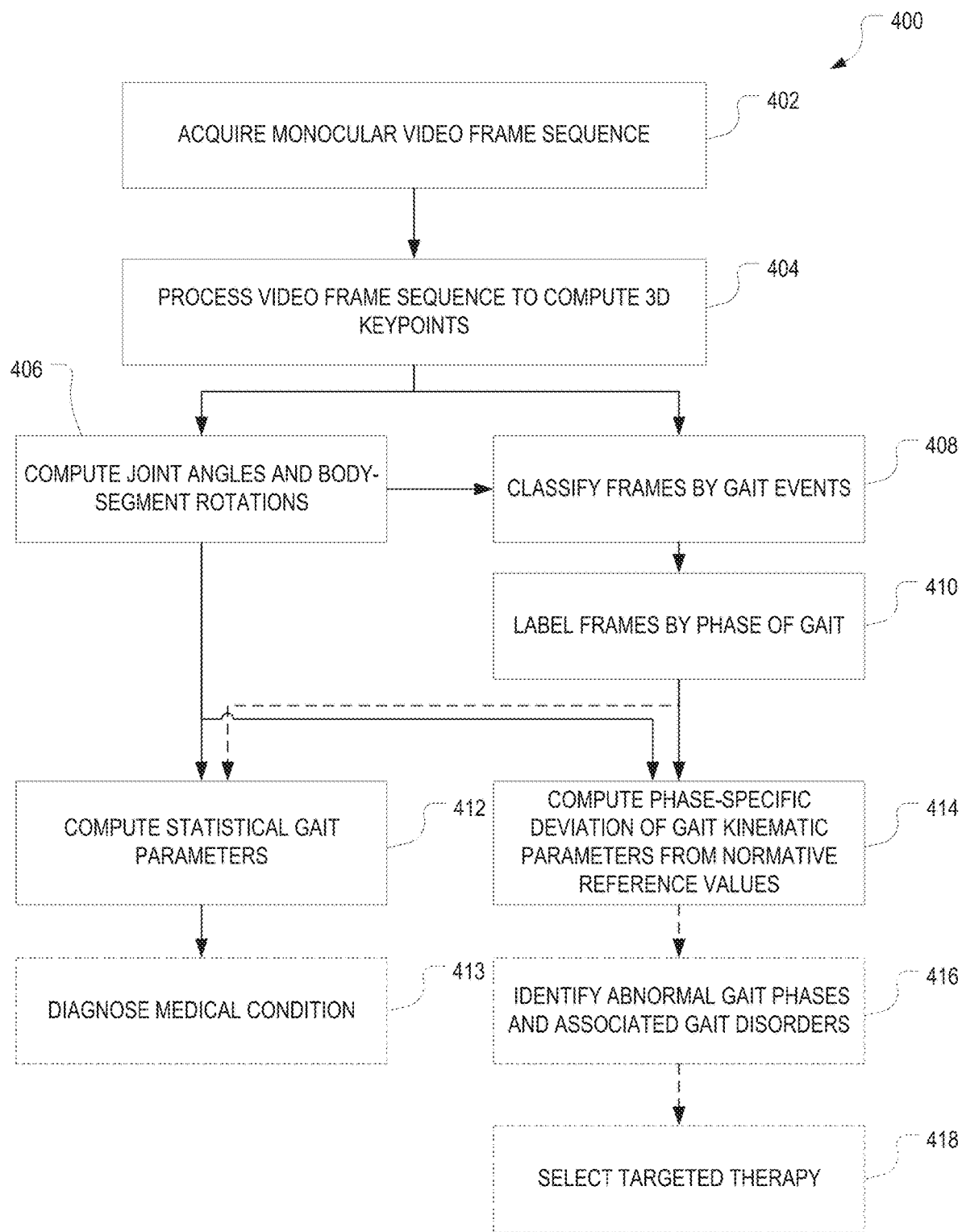
FIG. 4 is a flowchart illustrating methods for video-based gait characterization and analysis in accordance with various embodiments.

FIG. 4 is a flowchart illustrating methods 400 for video-based gait characterization and analysis in accordance with various embodiments. The methods begin with the acquisition of a monocular video frame sequence of a subject walking (402). The video frames are processed, e.g., in stages using the machine-learned 2D keypoint model 104 and 3D keypoint model 108 of the processing pipeline 100, to compute 3D keypoint coordinates for a set of anatomical keypoints associated with various joints and body segments (404). In one example, thirty-five 3D keypoints are predicted by the models. These 3D keypoints are then further processed, e.g., using the machine-learned gait models 130, 132, 160, to predict joint angles and/or body-segment rotations (406), and/or to detect gait events in the video frames and classify the frames accordingly (408). Some of the gait events, such as contact events associated with heel strikes and heel or toe lifting off the ground, may be predicted from the 3D keypoints, whereas other gait events, such as joints reaching their maximum angle during the gait cycle or body segments reaching certain specified orientations, can be derived from the joint angles and body-segment rotations. The classification of video frames based on occurrences of gait events may flow into the labeling of frames by the phase of the gait in the next step (410).

For further quantitative gait analysis, one or more statistical gait parameters, such as spatiotemporal parameters or various complex gait metrics (e.g., indicative of gait complexity, symmetry, variability, and/or overall quality) may be computed from the predicted joint angles and body-segment rotations (412). Computation of some statistical gait parameters may utilize certain gait events, e.g., to divide a longer time series of gait kinematic parameters into individual strides. In some embodiments, a medical condition can be diagnosed based on the statistical gait parameters (413), whether by a human user of the data or by an automated diagnosis tool. For example, complex gait metrics may flow into downstream predictive models that correlate gait to certain medical conditions, such as neurodegeneration (e.g., dementia, Alzheimer's, and others) and fall risk.

Alternatively or additionally, a temporally finer-grained gait analysis may be performed by computing, for one or more gait kinematic parameters (such as joint angles or body-segment rotations) of interest, an average deviation of the values of each parameter from normative reference values for each of one or more gait phases within the gait cycle (414). This phase-specific comparison between the subject's gait kinematic parameters and corresponding reference data, which may be obtained from gait measurements for a reference population, can serve to identify abnormal gait phases, and optionally diagnose associated gait disorders (416). In some embodiments, the identification of one or more abnormal gait phase(s) is used to then address the abnormality, e.g., by selecting a suitably targeted therapy, e.g., physiotherapy for the specific muscle(s) or muscle group(s) involved in the respective gait phase(s) (418).

Figure 5:
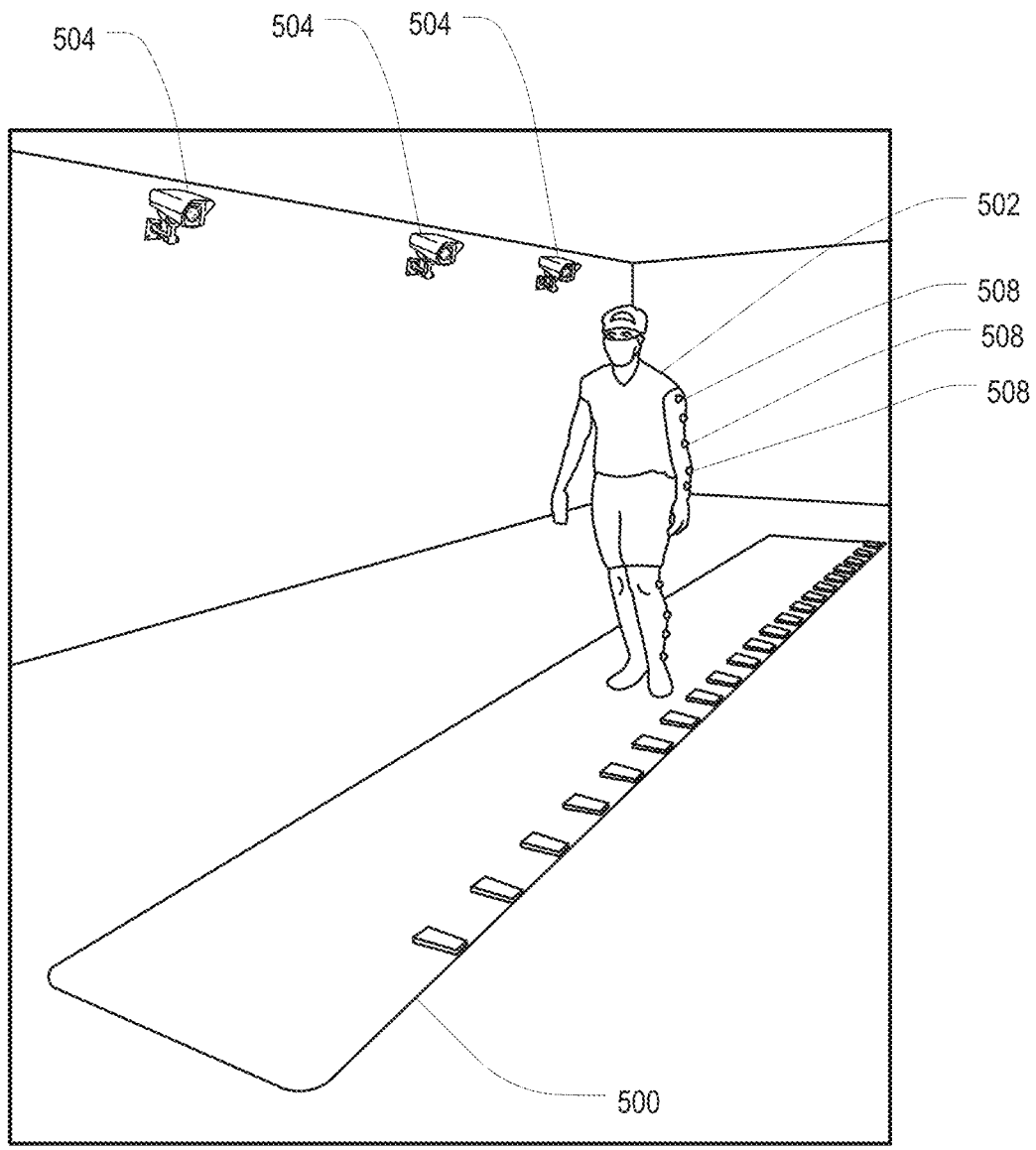
FIG. 5 is a schematic drawing of an example laboratory environment as may be used to obtain training data for the machine-learning models in the processing pipeline of FIG. 1.

FIG. 5 is a schematic drawing of an example laboratory environment as may be used to obtain training data for the machine-learning models in the processing pipeline of FIG. 1. The setup includes a GaitRITE mat or other pressure-sensitive walkway 500 in the center of the room for the subject 502 to walk down. Sensor embedded in the mat 500 are triggered by mechanical pressure, e.g., due to footfalls. As such, the mat 500 can generate ground-truth gait event data for use in training the gait event model. The mat 500 is surrounded by six cameras 504 (e.g., operating in the infrared or optical wavelength range), three to the left of the mat 500 (not shown) and three to the right as shown. The subject 502 walking on the mat 500 is equipped with motion capture markers 506, e.g., in some embodiments, 73 markers in total. The markers 506 may be passive, retroreflective markers detectable with infrared cameras. Alternatively, the markers 506 may be active markers with integrated light sources, such as light-emitting diodes (LEDs), which can be detected with optical cameras. The markers are precisely placed on the human body, e.g., near joints and other anatomical keypoints of interest. Together, the markers 506 and cameras 504, along with suitable computing hardware and software to process the camera outputs, constitute a marker-based motion capture system adapted for human pose measurements. More specifically, by processing synchronous video streams acquired by the cameras 504, the 3D coordinates of the markers themselves can be determined. With sufficient markers, this data, in turn, allows generating the ground-truth 3D keypoints and gait kinematic parameters for training the 3D keypoint model, body-segment rotation model, and joint angle model. An example marker-based motion captures system suited for obtaining the ground-truth data for training the processing pipeline 100 is the Vicon® motion capture system.

To obtain the sequence of video frames that serve as input to the processing pipeline, the laboratory setup further includes an additional single camera, generally of the same or similar type as subsequently used in the inference phase to acquire the monocular video input. FIG. 5 does not depict this camera, but rather, shows the walkway 500 from the viewpoint of the camera. As can be seen, the camera is generally positioned and oriented to view the walkway 500 at an angle. To properly associate inputs and outputs in the training data, the data streams from the cameras 504 of the motion capture system and from the pressure-sensitive walkway 500 are synchronized with a corresponding data stream from the single camera. While not strictly necessary, it is beneficial and convenient to also synchronize the cameras 504 of the motion capture system and the pressure-sensitive walkway 500 to each other and capture the data streams for the inputs and ground-truth outputs used in training the various machine-learning models of the processing pipeline all simultaneously.

Figure 6:
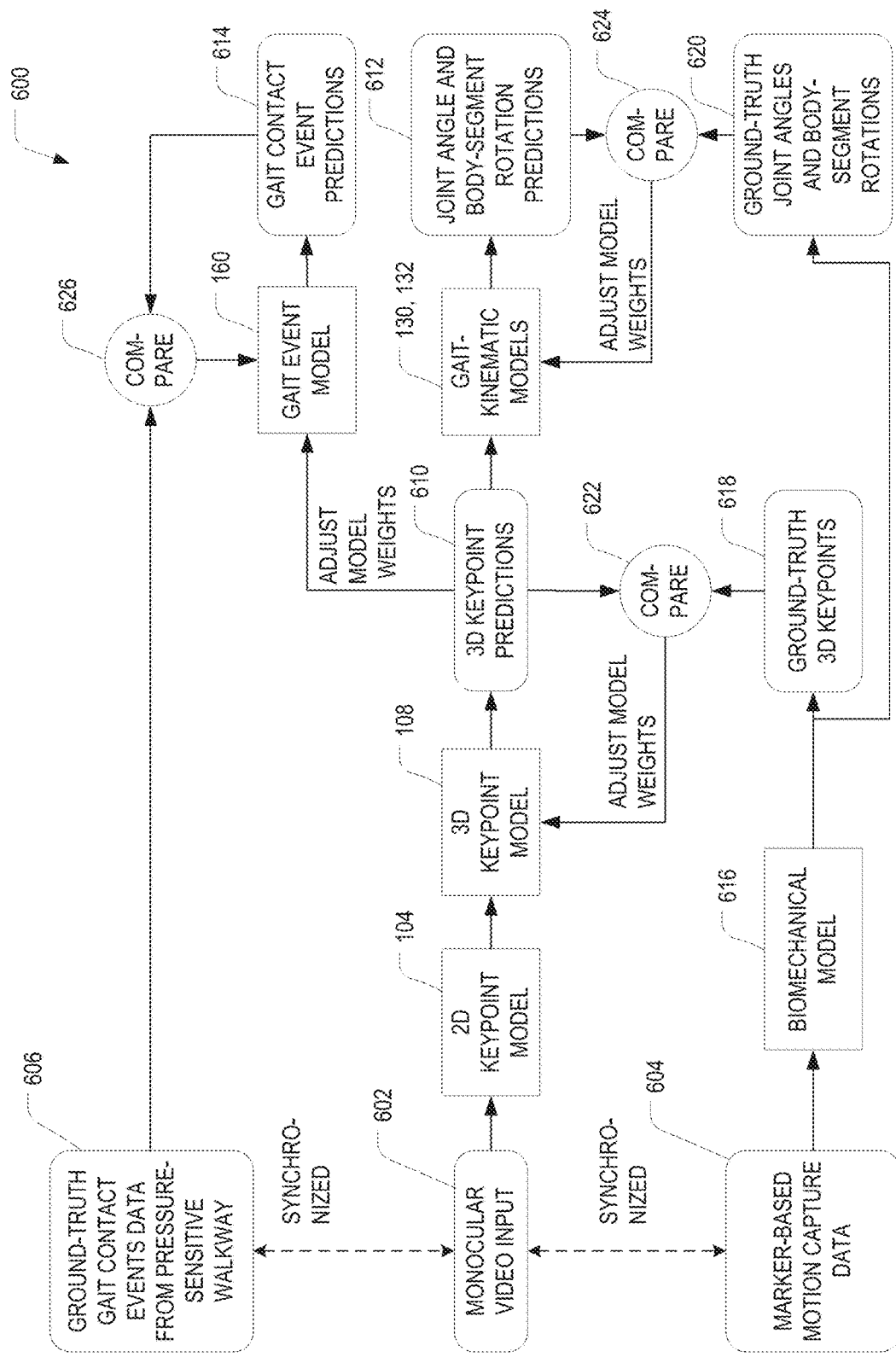
FIG. 6 is a block diagrams illustrating data flows during supervised training of various stages of the processing pipeline of FIG. 1, in accordance with various embodiments.

FIG. 6 is a block diagrams illustrating data flows during supervised training of various stages of the processing pipeline 100 of FIG. 1, in accordance with various embodiments. The inputs to the training process include the monocular video input 602 to the processing pipeline 100 and, synchronized therewith, marker-based motion capture data 604 and gait contact events data 606 obtained with a pressure-sensitive walkway. The video input 602 is processed by the 2D keypoint model 104 to compute (or, synonymously in the case of machine-learning models, "predict") 2D keypoints, which are in turn processed by the 3D keypoint model 108 to generate predictions of the 3D keypoints 610. At the next (third) stage of the processing pipeline, the 3D keypoint predictions 610 are input to gait kinematic models 130, 132 that predict body-segment rotations and joint angles 612, and to the gait event model 160 to provide gait contact event predictions 614.

The 2D keypoint model 104 at the first stage may be a pre-trained model whose model weights are not altered in the presently described training process. The 3D keypoint model 108, gait kinematic models 130, 132, and gait event model 160, on the other hand, are trained based on the input data 602, 604, 606 to the training process. The gait contact events data 604 serves as ground-truth outputs (or "labels") for training the gait event model 160. The marker-based motion capture data 604, which includes the 3D coordinates of the markers 506 placed on the subject during training data acquisition, is processed with a biomechanical model 616 to compute both ground-truth 3D keypoints 618 for the training of the 3D keypoint model 108, and ground-truth joint angles and body-segment rotations 620 for the training of the gait kinematic models 130, 132. The biomechanical model 616 is a computation model capturing the biomechanics of the body, e.g., including relative joint locations in a reference state and degrees of freedom of relative motion and associated ranges of motion. An example of a suitable biomechanical model available in an open-source implementation is the Conventional Gait Model (CGM) described by Leboeuf et al. in Gait Posture, 2019 March (http://pubmed.ncbi.nlm.nih.gov/3127876). The biomechanical model is capable of linking different locations on the body based on anatomical or physiological relations and constraints, and as such allows computing relevant anatomical keypoints, such as joint locations and mid-points or distinct locations on body segments, from the measured locations of the markers attached to the body. In many embodiments, the number of markers is significantly greater than the number of ground-truth 3D keypoints computed therefrom; in one example, coordinates of 73 markers result in 35 3D keypoints. The biomechanical model 616 also facilitates the computation of joint angles and body-segment rotations from the marker coordinates.

It is worth noting that the set of 3D keypoints computable from strategically placed markers exceeds the number of 3D keypoints that can be directly calculated (e.g., by triangulation, without machine-learning models) from the 2D keypoints identified in the video frames of marker-less multi-camera motion-capture systems. Likewise, the set of body-segment rotations and joint angles that can be determined, with the help of the biomechanical model 616, from the marker data, is generally larger than that obtainable from marker-less data. Thus, although the 3D keypoint model 108 can, in principle, be trained on training data required by various kinds of motion capture systems, use of marker-based training data is often beneficial.

In some embodiments, the training process involves first training the 3D keypoint model 108, and subsequently training, in any order, the gait-kinematic models 130, 132, and gait event model 160. In other embodiments, the machine-learning model pipeline may be trained end-to-end, that is, the model weights of the 3D keypoint, gait kinematic, and gait event models 108, 130, 132, 160 may all be updated within the same training iteration.

The 3D keypoint model 108 may be trained based on training data pairs that include, for each video frame, the 2D keypoints computed from the frame with the 2D keypoint models as the input, and ground-truth 3D keypoints 618 computed from the simultaneously acquired marker data as the corresponding output. The 3D keypoint predictions 610 computed for each 2D keypoint input are compared against the associated ground-truth 3D keypoints 618 (at 622), and based on a measure of the difference (generically understood as a deviation or discrepancy, for instance—but not necessarily—as expressed with a subtraction operation) between the predicted and ground-truth values, e.g., as captured in a suitable loss function, the model weights (e.g., neural network weights) of the 3D keypoint model 108 are adjusted. The prediction of 3D keypoints and computation of their difference from the ground-truth 3D keypoints 618 is then repeated for the next training data pair, and the process is repeated iteratively, e.g., until some convergence criterion has been met or a specified number of training iterations have been completed. Suitable learning algorithms for this iterative process of updating model weights are known to those of ordinary skill in the art, and include, e.g., back-propagation of errors with gradient descent for the training of neural network models. In some embodiments, one or more of the sub-models (e.g., the main body model) of the 3D keypoint model 108 may utilize pretrained weights from a public repository for transfer learning.

Similarly, the gait kinematic models 130, 132 may be trained on training data pairs that include, for each video frame, the 3D keypoints computed from the frame with the 2D and 3D keypoint models 104, 108 as the input, and ground-truth body-segment rotations and joint angles 620 computed from the simultaneously acquired marker data as the corresponding output. Based on comparisons (at 624), and measures of the differences, between predicted and ground-truth body segment rotations and joint angles 612, 620, the weights of the gait kinematic models 130, 132 can be iteratively adjusted.

The gait event model 160 may be trained on training data pairs that include, for each video frame, the 3D keypoints computed from the frame with the 2D and 3D keypoint models 104, 108 as the input, and ground-truth gait contact events data (labels) determined from simultaneously acquired footfall measurements as the corresponding output. Based on comparisons (at 626), and measures of the differences, between predicted and ground-truth gait contact events 614, 606, the weights of the gait event model 160 can be iteratively adjusted. In some embodiments, the output of the gait event model 160 is post-processed to eliminate false positives, e.g., by retaining only gait events with the highest probability. The accuracy of the gait event model can be quantified in terms of an average frame offset, defined as the mean of all differences between the frame numbers of frames classified for certain gait events in the ground-truth data and corresponding frames in the classifications generated by the model. Alternatively, the accuracy can be measured in terms of a milliseconds offset, defined as the mean of all differences between timestamps of the gait events as they occurred in the ground-truth data and the corresponding model predictions, respectively. In one example implementation of the above-described gait model, a frame offset of 0.85 (millisecond offset of 17.01 ms) for foot/toe off and a frame offset of 0.90 (millisecond offset of 17.97 ms) for foot/heel strike were achieved.

Accurate predictions of the 3D keypoints and downstream parameters by the machine-learning models from the monocular video input are contingent on the suitable placement of the camera, as well consistency of camera placement between training-data acquisition and use in the inference phase, that is, during deployment of the trained model. In general, the camera is oriented with its axis (defined normal to the sensor plane) in the horizontal plane at an angle relative to the walking path of the subject, as noted above. Beneficially, such a diagonal configuration provides visual information from coronal and sagittal planes of the subject simultaneously. The angle may, e.g., be between 15° and 25°; in one embodiment, 21° were determined to be optimal.

Figure 7A:
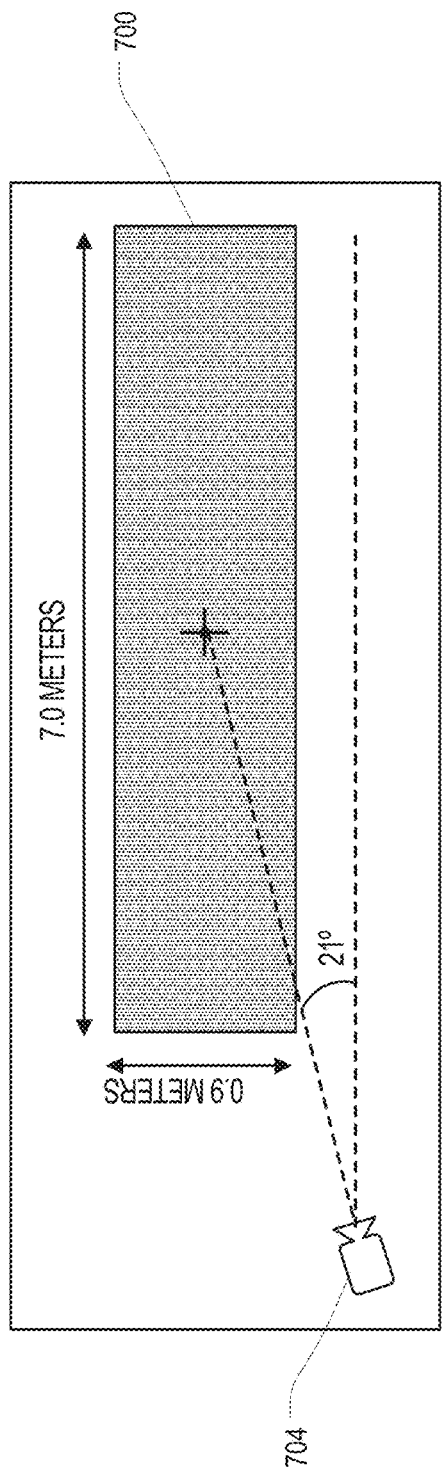
FIGS. 7A and 7B are schematic top and side views, respectively, of a walking surface and camera configuration utilized to acquire video input to the processing pipeline of FIG. 1 during deployment, in accordance with one embodiment.
Figure 7B:
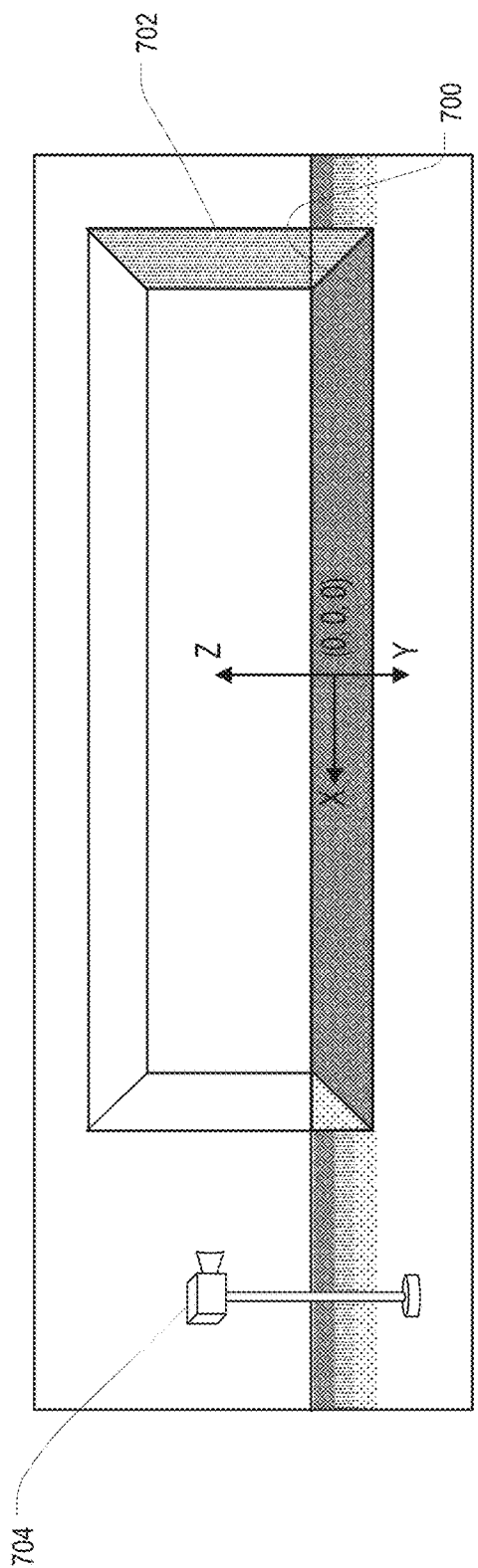

FIGS. 7A and 7B are schematic top and side views, respectively, of a walking surface and camera configuration utilized to acquire video input to the processing pipeline of FIG. 1 during deployment, in accordance with one embodiment. As shown in FIG. 7A, the rectangular walking surface 700 defines a high-aspect ratio area with a length of several meters and a width on the order of one meter, e.g., as depicted, an area 7 m long and 0.9 m wide. In use, the subject is instructed to walk within this area along its length from one end to the other, e.g., defining a walking path roughly corresponding to the longer center axis of the rectangle. The length of the walking path is chosen to encompass a number of strides sufficient for meaningful gait-based analysis, and the width is sufficient to ensure that the subject stays wholly within the defined area. Unlike a pressure-sensitive walkway, the walking surface 700 need not be equipped with any special physical structures, but may simply be a defined area of an existing floor, for example. However, in various embodiments, it may be beneficial to guide the subject with visual markings of the perimeter of the walking surface 700 (e.g., a chalk or masking tape outline).

FIG. 7B illustrates, in side view, a cubical volume, herein the "walking volume" 702, defined above the walking surface 700 and extending from the walking surface (that is, the floor) to a height suitable to contain the subject entirely within the volume 702 along the entire walking path, e.g., a height of 2 m (for human subjects). The walking volume 702 may be described within a 3D world coordinate system, e.g., having its origin at the center of the walking surface 700, its x- and y-axes along the longer and shorter dimensions of the walking surface, and its z-axis in the direction of height above the walking surface 700, as depicted.

The camera 704 is generally placed at a height and distance from the walking surface that keeps, at the selected camera orientation, the entire walking volume 702 (and thus the walking subject) within its field of view, with the walking volume 702 preferably taking up a large fraction of the field of view to provide good resolution of the recorded movement. In one example, the camera is mounted about 1.5 m above the floor, e.g., on a tripod or similar stand.

To allow reproducing the configuration shown in FIGS. 7A and 7B between the training phase and the subsequent deployment of the camera 704 to acquire video input for use in the inference phase, the walking volume 702 as defined in the 3D world coordinate system is transformed to the camera coordinate system. In the camera coordinate system, the camera position, that is the position from which the walking volume 704 is seen, may serve as the origin, and the camera orientation may serve as a coordinate axis relative to which the orientation of the walking path is set. The transformation may utilize the extrinsic parameters of the camera employed for collecting the training data, such as the 3D camera position relative to the origin of the 3D world coordinate system, and the intrinsic parameters, such as the camera focal length, and the camera's principal point, which determines the angular extent of its field of view. Finally, in order to translate the configuration to the software environment in which the camera is used, the cubical walking volume 702 is projected into two dimensions, defining an outline that is, in the software, overlayed with the acquired video frames to indicate the walking volume 702 within the imaged scene.

Figure 8B:
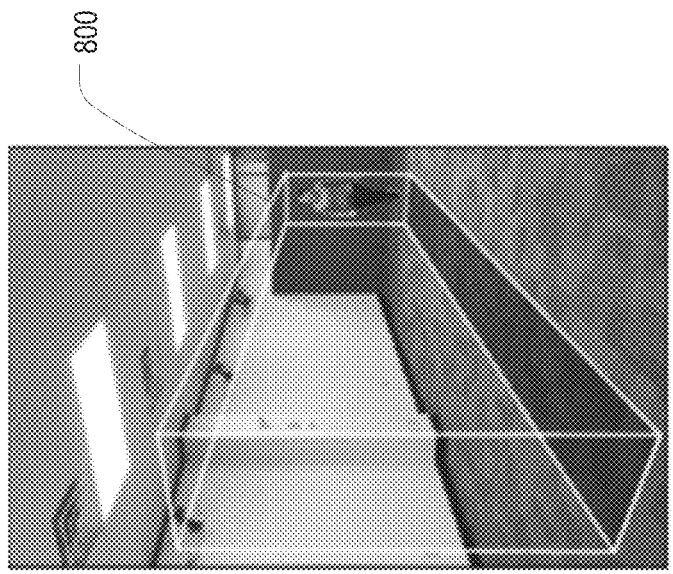
FIG. 8B shows an example of an actual camera frame, overlaid with an outline of the walking volume of FIG. 8A.
Figure 8A:
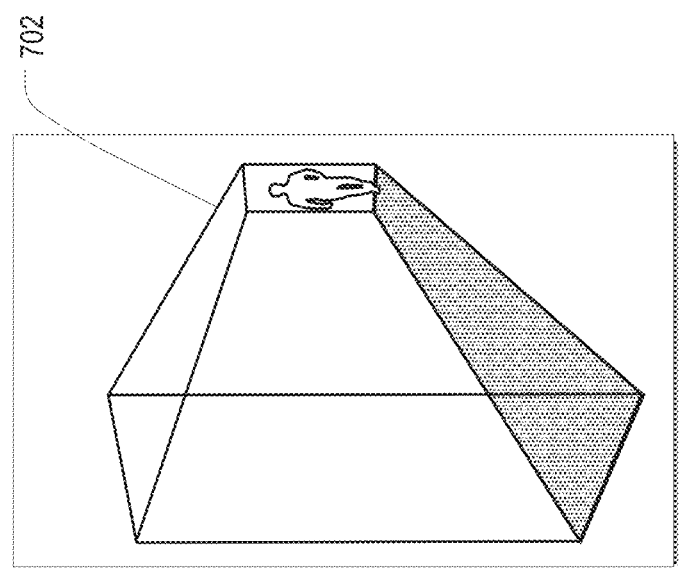
FIG. 8A is a schematic perspective view, from the point of view of the camera, of a walking volume defined above the walking surface of FIG. 7A, in accordance with one embodiment.

FIG. 8A is a schematic perspective view, from the point of view of the camera, of the walking volume 702. FIG. 8B shows an example of an actual camera frame, overlaid with an outline 800 of the walking volume 702 as results from the two-dimensional (2D) projection.

Once the walking volume in the camera coordinate system and/or its 2D projection onto the field of view have been defined and stored in software, they can be used to align the camera (e.g., the same camera as was used for acquisition of the training data, or another camera configurable for the same field of view) to a walking surface in a different environment, e.g., in a deployment environment, where video of a patient is acquired for processing by the machine-learning model(s) in the inference phase. In one embodiment, the placement and alignment process begins by placing the camera at approximately the same height as was used for acquisition of the training data (e.g., 1.5 m from the floor). Then, image acquisition (but not necessarily recording) with the camera is started within the software environment (e.g., within an app running on a mobile device), and the 2D outline 800 showing the 3D walking volume 702 in perspective view is overlaid onto the image. The camera position and orientation can now be adjusted to align the virtual walking surface defined by the base surface of the depicted walking volume with the actual walking surface 700, e.g., using edges of lateral walls for better alignment. For instance, the tilt of the camera may be adjusted until the vertical edges between walls are parallel to the vertical lines of the outline of the walking volume. In some embodiments, a walking surface of appropriate dimensions is marked on the floor, and the camera is adjusted until the marked walking surface coincides with the virtual walking surface in the camera view. In other embodiments, the actual walking surface is not defined a priori, but is determined to be the area of the floor within the camera view that is enclosed by the outline of the base surface. For visual guidance, the base surface may be aligned with existing markers in the real-world environment. For example, the walking surface as defined by the base surface may be aligned in parallel with the edges of the floor space defined by the walls. Optionally, the walking surface may be explicitly marked on the floor. Once the virtual walking surface and real walking surface are aligned, the subject is guided into position at one end of the walking surface, video recording by the camera is started, and the subject is instructed to walk in a direction towards the other end of the walking surface. It is important to ensure that the subject remains inside the walking volume throughout the process.

Figure 9A:
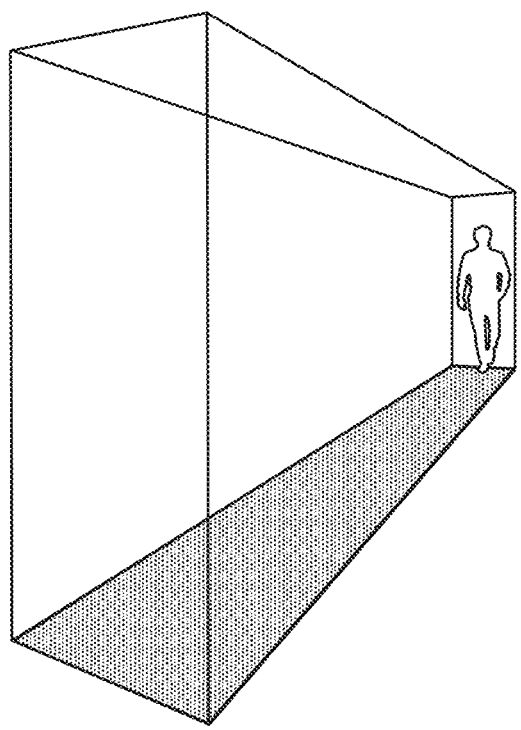
Figure 9B:
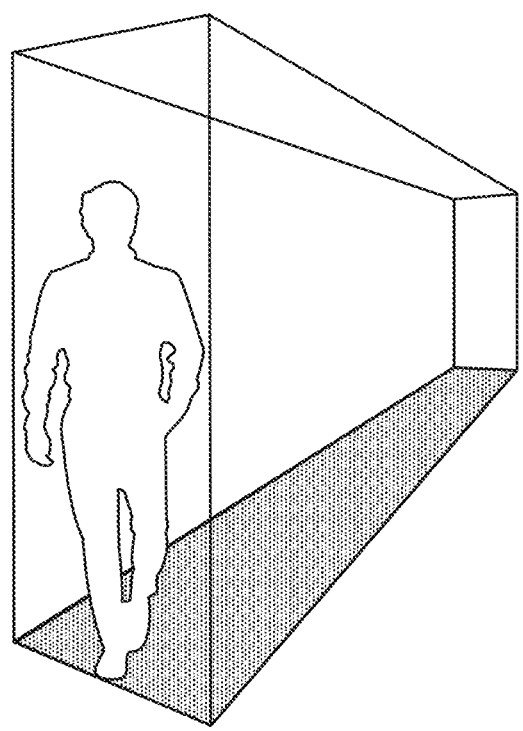
Figure 9C:
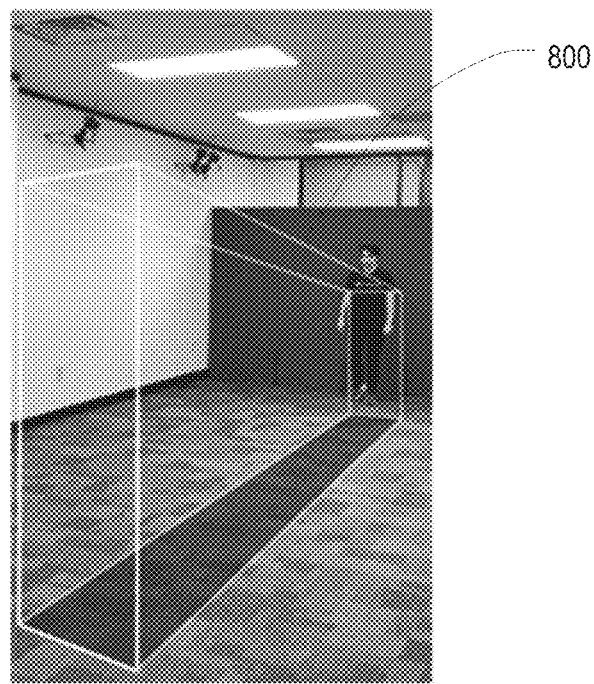
FIG. 9C shows an example of an actual camera frame overlaid with an outline of the walking volume, illustrating an example of camera misplacement.

FIGS. 9A and 9B are schematic perspective views illustrating the location of the subject relative to the walking volume at the beginning and end of an example walking path if the camera is properly aligned. Absent careful alignment, any misplacement of the camera 704 produces changes in position and orientation parameters utilized in the image processing that can result in errors of the computed results. FIG. 9C shows an example of an actual camera frame overlaid with an outline 800 of the walking volume 702, illustrating an example of camera misplacement. In this common scenario (among many possible scenarios), the camera is placed too close to the subject, which renders the appearance of the subject in the image too large as compared with the walking volume, and consequently causes the subject to be in part outside of the boundaries of the walking volume. Since the position of the camera now does not replicate the actual position of the camera used during training, the results of processing the video will be inaccurate.

In various embodiments, the video of the walking subject is acquired with the camera of a smartphone, electronic tablet, or similar mobile device, which displays the video on-screen as it is being acquired. The device may store a software application (or "app") that serves to guide the user through the alignment process, e.g., with the help of an outline of the 3D walking volume that is overlaid onto the video, as discussed above. In addition, the software application (or a separate application) may visualize various results of processing the video data, e.g., in the form of graphs, text, overlays only the video stream, or animations. The video processing may be performed locally on the mobile device, using its own processors, to the extent processing power permits. Alternatively, the video may be streamed over a mobile connection to a separate computer or computer cluster, e.g., a server or server group implementing a cloud-based web service, and outputs of the processing pipeline, such as the 3D keypoint coordinates, joint angles and body-segment rotations, gait event classifications and gait-phase labels may be sent back to the mobile device, where the data can be further processed for various visualizations and assembled into various user interfaces. Of course, the functionality of the processing pipeline 100 may also be distributed between the mobile device and one or more remote computers in various ways.

Figure 10:
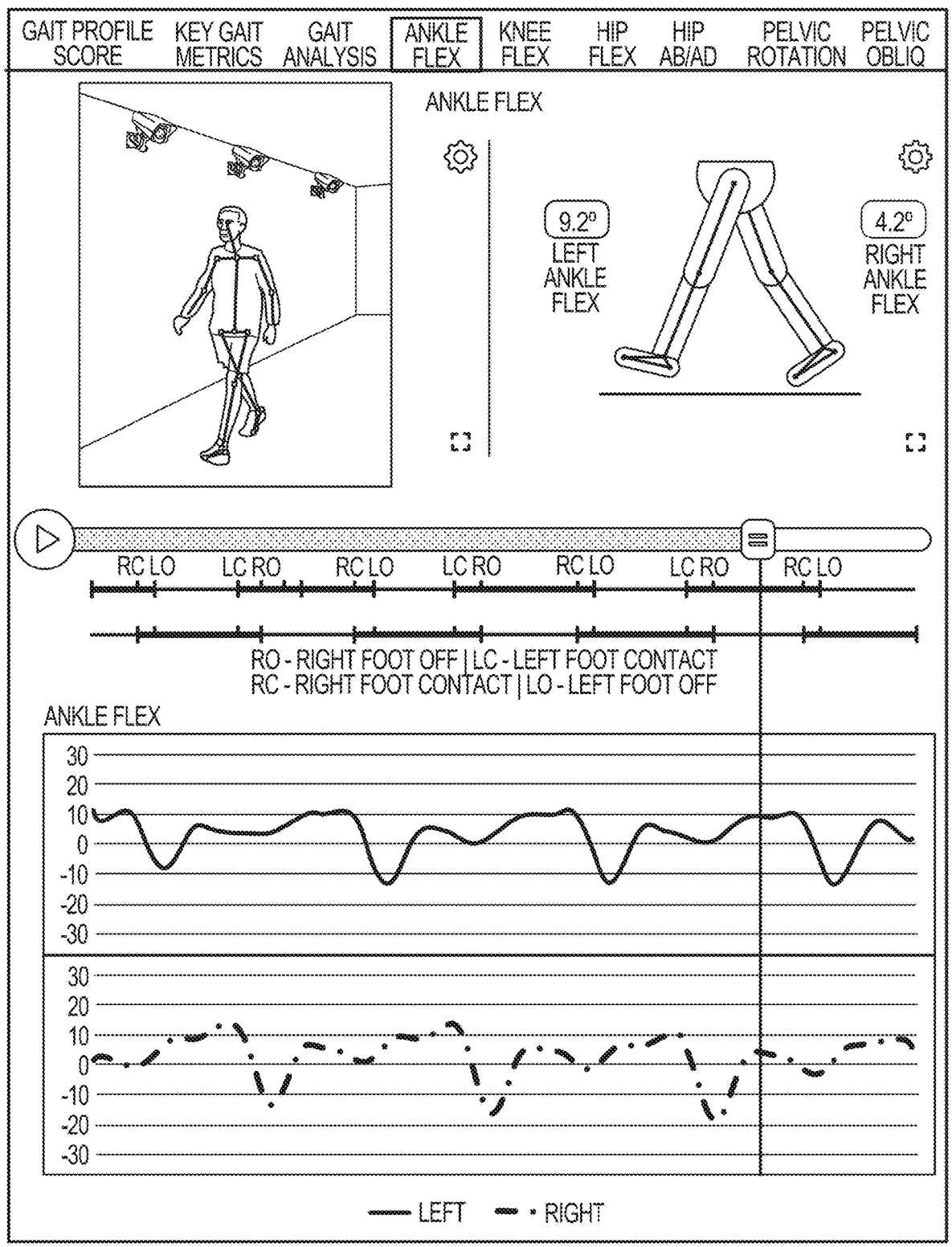
FIG. 10 is an example user interface as may be shown on the display of the mobile device.

FIG. 10 is an example user interface as may be shown on the display of the mobile device. As can be seen, the user interface includes a region showing the video of the walking subject, which may be live video or a recording. Overlaid onto the subject in the video may be a skeleton outline that identifies the instantaneous locations of various 2D keypoints computed in the processing pipeline. Another region of the user interface may display graphs of one or more selected time-dependent gait kinematic parameters, e.g., in the example shown, the flexion angles of the left and right ankles. The user interface may include multiple different tabs for different joints or body segments, or other means of allowing the user to select which gait kinematic parameter to display. Once the video capturing the entire walking path has been recorded, the graph may include the full associated time series for the selected gait kinematic parameter(s). Along with the graph, various identified gait phases may be displayed, e.g., in the form of a bar (located above the graph) that shows the demarcations, corresponding to certain gait events, between the gait phases. Further, as the recorded video is replayed, a video progress bar temporally aligned with the graph may show the instantaneous time within the video. A progress indicator line in the graph may move along with the progress indicator on the progress bar, clearly showing the instantaneous values of the gait kinematic parameters correlated with the video frames. The software application on the mobile device may, further, produce an animation, e.g., in the form of a moving skeleton figure, of at least part of the walking subject, e.g., the lower extremities, from the recorded video and relevant keypoint coordinates, body-segment rotations, and/or joint angles. The animation may be a multi-plane animation, e.g., including three videos in which the skeleton figures appears projected into the coronal, sagittal, and transverse planes. The animation, or a selected plane thereof, may be displayed in yet another region of the user interface, optionally in conjunction with numerical values of the gait-kinematic parameters of interest. In FIG. 10, the lower extremities are shown in the sagittal plane, with values of the instantaneous left and right ankle flexion angles. The user interface may include additional tabs that display aggregate gait data, such as multiple spatiotemporal gait metrics, gait profile scores, and other information.

Figure 11:
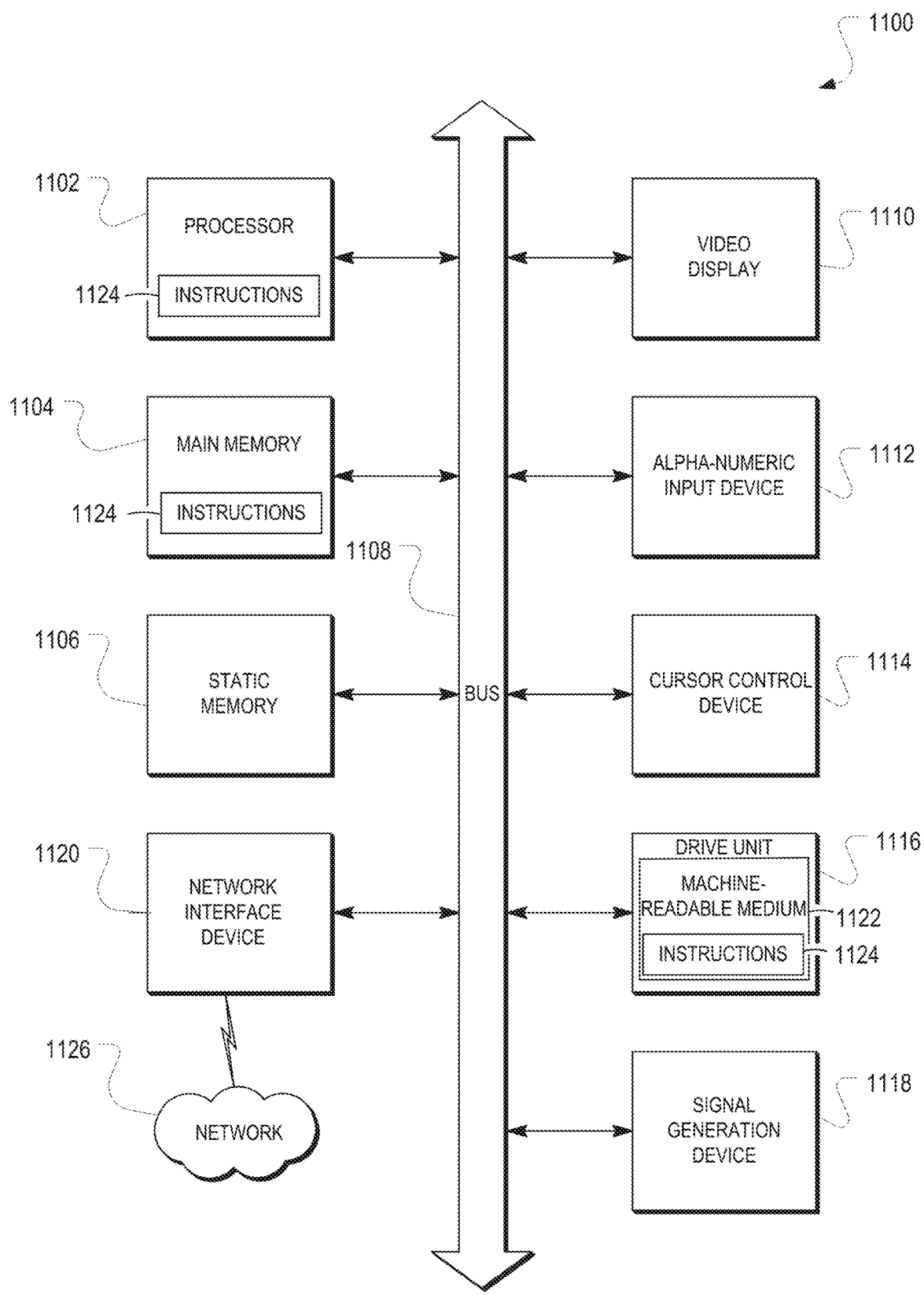
FIG. 11 is a block diagram of a machine in the example form of a computer system within which instructions for causing the machine to perform any one or more of the processing methods discussed herein may be executed.

FIG. 11 is a block diagram of a machine in the example form of a computer system 1100 within which instructions for causing the machine to perform any one or more of the processing methods discussed herein may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. While only a single machine is illustrated, the term "machine" shall also be taken to include any collection of machines that individually or jointly execute a set (or multiple sets) of instructions to perform any one or more of the processing methods (understood to include data visualization) discussed herein. For example, those of ordinary skill in the art will understand that the various processing modules and models depicted in FIG. 1, the alignment tool explained with reference to FIGS. 8A-9C, and the visualization functionality illustrated in FIG. 10, may be distributed over multiple computing devices, such as a mobile device facilitating camera alignment and results visualization, and a remote server computer performing the video processing.

The example computer system 1100 includes one or more processors 1102 (e.g., a central processing unit (CPU), a graphics processing unit (GPU) or both), a main memory 1104 and a static memory 1106, which communicate with each other via a bus 1108. The computer system 1100 may further include a video display unit 1110 (e.g., a liquid crystal display (LCD) or a cathode ray tube (CRT)). The computer system 1100 also includes an alphanumeric input device 1112 (e.g., a keyboard), a user interface (UI) navigation device 1114 (e.g., a mouse), a disk drive unit 1116, a signal generation device 1118 (e.g., a speaker), a network interface device 1120, and a data interface device 1128 (such as, e.g., a camera interface).

The disk drive unit 1116 includes a machine-readable medium 1122 storing one or more sets of instructions and data structures (e.g., software) 1124 embodying or utilized by any one or more of the methodologies or functions described herein. The instructions 1124 may also reside, completely or at least partially, within the main memory 1104 and/or within the processor 1102 during execution thereof by the computer system 1100, the main memory 1104 and the processor 1102 also constituting machine-readable media.

While the machine-readable medium 1122 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; CD-ROM and DVD-ROM disks, or other data-storage devices. Further, the term "machine-readable medium" shall be taken to include a non-tangible signal or transmission medium, including an electrical signal, a magnetic signal, an electromagnetic signal, an acoustic signal and an optical signal.

Although the inventive subject matter has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method comprising:
obtaining a monocular video of a subject walking;
processing the monocular video to determine, in multiple video frames of the monocular video, two-dimensional (2D) keypoint coordinates for a first set of anatomical keypoints of the subject;
processing the 2D keypoint coordinates for the first set of anatomical keypoints with a 3D keypoints model comprising one or more machine-learning models to determine, in the multiple video frames, three-dimensional (3D) keypoint coordinates for a second set of anatomical keypoints of the subject;
processing the 3D keypoint coordinates for the second set of anatomical keypoints with one or more gait models comprising one or more machine-learning models to determine, for the multiple video frames, classifications of gait contact events and at least one of joint angles or body-segment rotation angles,
labeling the multiple video frames by gait phase based on the classifications of the gait contact events and of additional gait events derived from the joint angles or body-segment rotation angles, wherein the gait contact events and additional gait events demarcate gait phases within individual gait cycles;
computing, based on the labeling by gait phase, phase-specific deviations of one or more of the joint angles or body-segment rotation angles from respective reference data for the one or more of the joint angles or body-segment rotation angles;
identifying one or more abnormal gait phases based on the phase-specific deviations, and
outputting at least one of the joint angles or body-segment rotations angles or the classifications of the gait events to a user interface displayed on an electronic device for selection of a treatment targeted at one or more muscles associated with the one or more abnormal gait phases.

2. The method of claim 1, wherein the video is processed using one or more pre-trained machine-learning models to compute the 2D keypoint coordinates for the first set of anatomical keypoints.

3. The method of claim 1, wherein the second set of anatomical keypoints includes at least one anatomical keypoint not included in the first set of anatomical keypoints.

4. The method of claim 1, wherein the second set of anatomical keypoints comprises keypoints associated with left and right anterior pelvis and left and right posterior pelvis.

5. The method of claim 1, wherein the second set of anatomical keypoints comprises keypoints associated with left and right heel, foot, lateral ankle, first metatarsal, and fifth metatarsal.

6. The method of claim 1, wherein the one or more machine-learning models of the 3D keypoint model have been trained on a training video of a training subject walking in conjunction with ground-truth 3D keypoint coordinates of the second set of anatomical keypoints computed from physical marker data synchronized with the training video.

7. The method of claim 6, wherein:
the physical marker data comprises 3D marker coordinates of a set of physical markers attached to the training subject, the 3D marker coordinates computed from videos of the physical markers acquired by multiple cameras simultaneously and synchronously with the training video; and
the ground-truth 3D keypoint coordinates are computed from the 3D marker coordinates using a biomechanical model.

8. The method of claim 6, wherein the physical markers exceed the ground-truth 3D keypoint coordinates computed therefrom in number.

9. The method of claim 1, wherein:
the one or more gait models comprise one or more machine-learning models to determine the at least one of joint angles or body-segment rotation angles that have been trained on a training video of a training subject walking in conjunction with associated ground-truth joint angles or ground-truth body-segment rotation angles computed from physical marker data synchronized with the training video.

10. The method of claim 9, wherein:
the physical marker data comprises 3D marker coordinates of a set of physical markers attached to the training subject, the 3D marker coordinates computed from videos of the physical markers acquired by multiple cameras simultaneously and synchronously with the training video; and
the ground-truth joint angles or ground-truth body-segment rotation angles are computed from the 3D marker coordinates using a biomechanical model.

11. The method of claim 1, wherein:
the one or more gait models comprise a machine-learning model to determine the classifications of the gait contact events for the multiple video frames, the machine-learning model having been trained on a training video of a training subject walking in conjunction with associated ground-truth gait contact event classifications obtained with a pressure-sensitive walkway.

12. The method of claim 1, wherein the clinical condition comprises a gait abnormality or disorder.

13. The method of claim 1, wherein the clinical condition comprises at least one of: neurodegeneration, heightened fall risk, movement dysfunction, or injury.

14. The method of claim 1, further comprising outputting at least one of the joint angles, body-segment rotations angles, or classifications of gait events to the user interface for monitoring efficacy of the treatment.

15. One or more non-transitory machine-readable media storing instructions which, when executed by one or more computer processors, cause the one or more computer processors to process a monocular video of a subject walking by performing operations comprising:
- processing the video to determine, in multiple video frames, two-dimensional (2D) keypoint coordinates for a first set of anatomical keypoints of the subject;
- processing the 2D keypoint coordinates for the first set of anatomical keypoints with a 3D keypoints model comprising one or more machine-learning models to determine, in the multiple video frames, three-dimensional (3D) keypoint coordinates for a second set of anatomical keypoints of the subject; and
- processing the 3D keypoint coordinates for the second set of anatomical keypoints with one or more gait models comprising one or more machine-learning models to determine, for the multiple video frames, classifications of gait contact events and at least one of joint angles or body-segment rotation angles;
- labeling the multiple video frames by gait phase based on the classifications of the gait contact events and of additional gait events derived from the joint angles or body-segment rotation angles, wherein the gait contact events and additional gait events demarcate gait phases within individual gait cycles;
- computing, based on the labeling by gait phase, phase-specific deviations of one or more of the joint angles or body-segment rotation angles from respective reference data for the one or more of the joint angles or body-segment rotation angles;
- identifying one or more abnormal gait phases based on the phase-specific deviations; and
- causing an output of at least one of the joint angles or body-segment rotation angles or the classifications of the gait events to a user interface displayed on an electronic device for selection of a treatment targeted at one or more muscles associated with the one or more abnormal gait phases.

* * * * *